US009750568B2

(12) United States Patent
Sobotka

(10) Patent No.: US 9,750,568 B2
(45) Date of Patent: Sep. 5, 2017

(54) OVARIAN NEUROMODULATION AND ASSOCIATED SYSTEMS AND METHODS

(71) Applicants: MEDTRONIC ARDIAN LUXEMBOURG S.A.R.L., Luxembourg (LU); Paul Sobotka, West St. Paul, MN (US)

(72) Inventor: Paul Sobotka, West St. Paul, MN (US)

(73) Assignee: Medtronic Ardian Luxembourg S.a.r.l., Luxembourg (LU)

(*) Notice: Subject to any disclaimer, the term of this patent is extended or adjusted under 35 U.S.C. 154(b) by 277 days.

(21) Appl. No.: 14/379,890

(22) PCT Filed: Mar. 7, 2013

(86) PCT No.: PCT/US2013/029690
§ 371 (c)(1),
(2) Date: Aug. 20, 2014

(87) PCT Pub. No.: WO2013/134548
PCT Pub. Date: Sep. 12, 2013

(65) Prior Publication Data
US 2015/0051594 A1 Feb. 19, 2015

Related U.S. Application Data

(60) Provisional application No. 61/608,452, filed on Mar. 8, 2012.

(51) Int. Cl.
A61B 18/04 (2006.01)
A61B 18/14 (2006.01)
(Continued)

(52) U.S. Cl.
CPC .......... A61B 18/1492 (2013.01); A61B 18/02 (2013.01); A61B 18/04 (2013.01);
(Continued)

(58) Field of Classification Search
CPC ...... A61B 2018/00559; A61B 18/1492; A61B 2018/00577; A61B 2018/0212; A61B 2018/00434
See application file for complete search history.

(56) References Cited

U.S. PATENT DOCUMENTS 4,602,624 A 7/1986 Naples et al.
4,649,936 A 3/1987 Ungar et al.
(Continued)

FOREIGN PATENT DOCUMENTS

CN 103096826 5/2013
EP 0737487 10/1996
(Continued)

OTHER PUBLICATIONS

Saksouk, F.A., Johson, S.C. Recognition of the Ovaries and Ovarian Origin of Pelvic Masses with CT. 2004. RadioGraphics; 24:S133-S146.*
(Continued)

Primary Examiner — Jaymi Della
Assistant Examiner — Eunhwa Kim

(57) ABSTRACT

Methods for treating polycystic ovary syndrome with therapeutic ovarian neuromodulation and associated systems and methods are disclosed herein. Polycystic ovary syndrome can be associated, for example, with a condition including at least one of oligo/amenorrhea, infertility, hirsutism, obesity, metabolic syndrome, insulin resistance, and increased cardiovascular risk profile. One aspect of the present technology is directed to methods that at least partially inhibit sympathetic neural activity in nerves proximate an ovarian artery of an ovary of a patient. Sympathetic drive in the patient can thereby be reduced in a manner that treats the patient for the polycystic ovary syndrome. Ovarian sympathetic nerve activity can be modulated along afferent and/or efferent pathways. The modulation can be achieved, for (Continued)

example, using an intravascularly positioned catheter carrying a therapeutic assembly, e.g., a therapeutic assembly configured to use electrically-induced, thermally-induced, and/or chemically-induced approaches to modulate the ovarian nerve.

22 Claims, 10 Drawing Sheets

(51) Int. Cl.
    *A61N 1/36*     (2006.01)
    *A61B 18/00*     (2006.01)
    *A61B 18/02*     (2006.01)

(52) U.S. Cl.
    CPC ...... *A61N 1/36057* (2013.01); *A61N 1/36117* (2013.01); *A61B 2018/00404* (2013.01); *A61B 2018/00434* (2013.01); *A61B 2018/00559* (2013.01); *A61B 2018/00577* (2013.01); *A61B 2018/0212* (2013.01)

(56) References Cited

U.S. PATENT DOCUMENTS

| | | |
|---|---|---|
| 4,709,698 A | 12/1987 | Johnston et al. |
| 4,764,504 A | 8/1988 | Johnson et al. |
| 4,890,623 A | 1/1990 | Cook et al. |
| 4,976,711 A | 12/1990 | Parins et al. |
| 5,037,391 A | 8/1991 | Hammerslag et al. |
| 5,170,803 A | 12/1992 | Hewson et al. |
| 5,203,772 A | 4/1993 | Hammerslag et al. |
| 5,300,068 A | 4/1994 | Rosar et al. |
| 5,322,064 A | 6/1994 | Lundquist |
| 5,358,514 A | 10/1994 | Schulman et al. |
| 5,368,591 A | 11/1994 | Lennox et al. |
| 5,415,633 A | 5/1995 | Lazarus et al. |
| 5,423,744 A | 6/1995 | Gencheff et al. |
| 5,425,364 A | 6/1995 | Imran |
| 5,437,288 A | 8/1995 | Schwartz et al. |
| 5,457,109 A * | 10/1995 | Antonucci ............ A61K 31/41 514/253.1 |
| 5,484,400 A | 1/1996 | Edwards et al. |
| 5,487,757 A | 1/1996 | Truckai et al. |
| 5,571,147 A | 11/1996 | Sluijter et al. |
| 5,588,964 A | 12/1996 | Imran et al. |
| 5,599,345 A | 2/1997 | Edwards et al. |
| 5,626,576 A | 5/1997 | Janssen |
| 5,658,278 A | 8/1997 | Imran et al. |
| 5,672,174 A | 9/1997 | Gough et al. |
| 5,688,266 A | 11/1997 | Edwards et al. |
| 5,700,282 A | 12/1997 | Zabara |
| 5,707,400 A | 1/1998 | Terry, Jr. et al. |
| 5,766,167 A | 6/1998 | Eggers et al. |
| 5,772,590 A | 6/1998 | Webster, Jr. |
| 5,800,432 A | 9/1998 | Swanson |
| 5,843,152 A | 12/1998 | Tu et al. |
| 5,860,974 A | 1/1999 | Abele et al. |
| 5,865,787 A | 2/1999 | Shapland et al. |
| 5,893,885 A | 4/1999 | Webster et al. |
| 5,899,898 A | 5/1999 | Arless et al. |
| 5,944,710 A | 8/1999 | Dev et al. |
| 5,954,719 A | 9/1999 | Chen et al. |
| 5,983,141 A | 11/1999 | Sluijter et al. |
| 6,004,269 A | 12/1999 | Crowley et al. |
| 6,009,877 A | 1/2000 | Edwards |
| 6,024,740 A | 2/2000 | Lesh et al. |
| 6,036,687 A | 3/2000 | Laufer et al. |
| 6,066,134 A | 5/2000 | Eggers et al. |
| 6,091,995 A | 7/2000 | Ingle et al. |
| 6,099,524 A | 8/2000 | Lipson et al. |
| 6,106,518 A | 8/2000 | Wittenberger et al. |
| 6,117,101 A | 9/2000 | Diederich et al. |
| 6,135,999 A | 10/2000 | Fanton et al. |
| 6,142,993 A | 11/2000 | Whayne et al. |
| 6,149,620 A | 11/2000 | Baker et al. |
| 6,161,048 A | 12/2000 | Sluijter et al. |
| 6,219,577 B1 | 4/2001 | Brown, III et al. |
| 6,224,592 B1 | 5/2001 | Eggers et al. |
| 6,246,912 B1 | 6/2001 | Sluijter et al. |
| 6,273,886 B1 | 8/2001 | Edwards et al. |
| 6,283,951 B1 | 9/2001 | Flaherty et al. |
| 6,292,695 B1 | 9/2001 | Webster, Jr. et al. |
| 6,314,325 B1 | 11/2001 | Fitz |
| 6,322,558 B1 | 11/2001 | Taylor et al. |
| 6,322,559 B1 | 11/2001 | Daulton et al. |
| 6,405,732 B1 | 6/2002 | Edwards et al. |
| 6,413,255 B1 | 7/2002 | Stern |
| 6,425,867 B1 | 7/2002 | Vaezy et al. |
| 6,488,679 B1 | 12/2002 | Swanson et al. |
| 6,506,189 B1 | 1/2003 | Rittman, III et al. |
| 6,514,226 B1 | 2/2003 | Levin et al. |
| 6,522,926 B1 | 2/2003 | Kieval et al. |
| 6,542,781 B1 | 4/2003 | Koblish et al. |
| 6,562,034 B2 | 5/2003 | Edwards et al. |
| 6,616,624 B1 | 9/2003 | Kieval |
| 6,622,731 B2 | 9/2003 | Daniel et al. |
| 6,635,054 B2 | 10/2003 | Fjield et al. |
| 6,640,120 B1 | 10/2003 | Swanson et al. |
| 6,685,648 B2 | 2/2004 | Flaherty et al. |
| 6,711,444 B2 | 3/2004 | Koblish |
| 6,736,835 B2 | 5/2004 | Pellegrino et al. |
| 6,752,805 B2 | 6/2004 | Maguire et al. |
| 6,845,267 B2 | 1/2005 | Harrison et al. |
| 6,850,801 B2 | 2/2005 | Kieval et al. |
| 6,869,431 B2 | 3/2005 | Maguire et al. |
| 6,885,888 B2 | 4/2005 | Rezai |
| 6,887,235 B2 | 5/2005 | O'Connor et al. |
| 6,893,436 B2 | 5/2005 | Woodard et al. |
| 6,917,834 B2 | 7/2005 | Koblish et al. |
| 6,923,808 B2 | 8/2005 | Taimisto et al. |
| 6,939,346 B2 | 9/2005 | Kannenberg et al. |
| 6,949,097 B2 | 9/2005 | Stewart et al. |
| 6,978,174 B2 | 12/2005 | Gelfand et al. |
| 7,149,574 B2 | 12/2006 | Yun et al. |
| 7,162,303 B2 | 1/2007 | Levin et al. |
| 7,221,979 B2 | 5/2007 | Zhou et al. |
| 7,381,200 B2 | 6/2008 | Katoh et al. |
| 7,390,894 B2 | 6/2008 | Weinshilboum et al. |
| 7,617,005 B2 | 11/2009 | Demarais et al. |
| 7,620,451 B2 | 11/2009 | Demarais et al. |
| 7,647,115 B2 | 1/2010 | Levin et al. |
| 7,653,438 B2 | 1/2010 | Deem et al. |
| 7,717,948 B2 | 5/2010 | Demarais et al. |
| 7,778,703 B2 | 8/2010 | Gross et al. |
| 8,131,371 B2 | 3/2012 | Demarals et al. |
| 8,131,372 B2 | 3/2012 | Levin et al. |
| 8,140,170 B2 | 3/2012 | Rezai et al. |
| 8,145,317 B2 | 3/2012 | Demarais et al. |
| 8,150,518 B2 | 4/2012 | Levin et al. |
| 8,150,519 B2 | 4/2012 | Demarais et al. |
| 8,150,520 B2 | 4/2012 | Demarais et al. |
| 8,175,711 B2 | 5/2012 | Demarais et al. |
| 8,728,075 B2 | 5/2014 | Wu et al. |
| 9,486,243 B2 | 11/2016 | Eskuri |
| 2002/0065515 A1 | 5/2002 | Falwell et al. |
| 2002/0065542 A1 | 5/2002 | Lax et al. |
| 2002/0128662 A1 | 9/2002 | Brock et al. |
| 2002/0139379 A1 | 10/2002 | Edwards et al. |
| 2002/0165532 A1 | 11/2002 | Hill et al. |
| 2002/0183682 A1 | 12/2002 | Darvish et al. |
| 2002/0198520 A1 | 12/2002 | Coen et al. |
| 2003/0050635 A1 | 3/2003 | Truckai et al. |
| 2003/0050681 A1 | 3/2003 | Pianca et al. |
| 2003/0055422 A1 | 3/2003 | Lesh |
| 2003/0060858 A1 | 3/2003 | Kieval et al. |
| 2003/0074039 A1 | 4/2003 | Puskas |
| 2003/0078644 A1 | 4/2003 | Phan |
| 2003/0109778 A1 | 6/2003 | Rashidi |
| 2003/0125720 A1 | 7/2003 | Woodward et al. |
| 2003/0125790 A1 | 7/2003 | Fastovsky et al. |
| 2003/0181897 A1 | 9/2003 | Thomas et al. |
| 2003/0199863 A1 | 10/2003 | Swanson et al. |

(56) References Cited

U.S. PATENT DOCUMENTS

| | | | |
|---|---|---|---|
| 2003/0212394 A1 | 11/2003 | Pearson et al. |
| 2003/0216792 A1 | 11/2003 | Levin et al. |
| 2003/0229340 A1 | 12/2003 | Sherry et al. |
| 2003/0233099 A1 | 12/2003 | Dansek et al. |
| 2004/0010289 A1 | 1/2004 | Biggs et al. |
| 2004/0073141 A1 | 4/2004 | Hartly et al. |
| 2004/0215186 A1 | 10/2004 | Cornelius et al. |
| 2005/0004644 A1 | 1/2005 | Kelsch et al. |
| 2005/0080409 A1 | 4/2005 | Young et al. |
| 2005/0096647 A1 | 5/2005 | Steinke et al. |
| 2005/0187455 A1 | 8/2005 | Rashidi |
| 2005/0187579 A1 | 8/2005 | Danek et al. |
| 2005/0228460 A1 | 10/2005 | Levin et al. |
| 2005/0240229 A1 | 10/2005 | Whitehurst et al. |
| 2005/0267010 A1 | 12/2005 | Goodson et al. |
| 2005/0288730 A1 | 12/2005 | Deem et al. |
| 2006/0079943 A1 | 4/2006 | Narciso |
| 2006/0085054 A1 | 4/2006 | Zikorus et al. |
| 2006/0095029 A1 | 5/2006 | Young et al. |
| 2006/0100618 A1 | 5/2006 | Chan et al. |
| 2006/0206150 A1 | 9/2006 | Demarais et al. |
| 2006/0271111 A1 | 11/2006 | Demarais et al. |
| 2007/0066878 A1 | 3/2007 | Worley et al. |
| 2007/0129720 A1 | 6/2007 | Demarais et al. |
| 2007/0135875 A1 | 6/2007 | Demarais et al. |
| 2007/0156131 A1 | 7/2007 | Datta |
| 2007/0173891 A1 | 7/2007 | Buras |
| 2007/0265687 A1 | 11/2007 | Deem et al. |
| 2008/0255642 A1 | 10/2008 | Zarins et al. |
| 2008/0319513 A1 | 12/2008 | Pu et al. |
| 2009/0024195 A1 | 1/2009 | Rezai et al. |
| 2009/0036948 A1 | 2/2009 | Levin et al. |
| 2009/0062873 A1 | 3/2009 | Wu et al. |
| 2009/0076409 A1 | 3/2009 | Wu et al. |
| 2010/0119482 A1 | 5/2010 | Yun et al. |
| 2010/0137700 A1* | 6/2010 | Passman ................. A61B 5/04 600/374 |
| 2010/0137860 A1 | 6/2010 | Demarais et al. |
| 2010/0137952 A1 | 6/2010 | Demarais et al. |
| 2010/0168731 A1 | 7/2010 | Wu et al. |
| 2010/0168739 A1 | 7/2010 | Wu et al. |
| 2010/0191112 A1 | 7/2010 | Demarais et al. |
| 2010/0222851 A1 | 9/2010 | Deem et al. |
| 2010/0222854 A1 | 9/2010 | Demarais et al. |
| 2010/0286684 A1 | 11/2010 | Hata et al. |
| 2010/0286734 A1 | 11/2010 | Yun et al. |
| 2011/0052718 A1 | 3/2011 | Rangel |
| 2011/0144468 A1 | 6/2011 | Boggs et al. |
| 2011/0264011 A1* | 10/2011 | Wu ........................ A61F 5/0013 601/2 |
| 2011/0264075 A1 | 10/2011 | Leung et al. |
| 2012/0116382 A1 | 5/2012 | Ku et al. |
| 2012/0130289 A1 | 5/2012 | Demarais et al. |
| 2012/0130345 A1 | 5/2012 | Levin et al. |
| 2012/0136350 A1 | 5/2012 | Goshgarian et al. |
| 2012/0150267 A1 | 6/2012 | Buckley et al. |
| 2012/0172837 A1 | 7/2012 | Demarais et al. |
| 2013/0144251 A1 | 6/2013 | Sobotka |

FOREIGN PATENT DOCUMENTS

| | | |
|---|---|---|
| EP | 2563255 | 3/2013 |
| WO | WO9407446 | 4/1994 |
| WO | WO-9525472 | 9/1995 |
| WO | WO9531142 | 11/1995 |
| WO | WO-9736548 | 10/1997 |
| WO | WO9842403 | 10/1998 |
| WO | WO-99/00060 | 1/1999 |
| WO | WO9900060 | 1/1999 |
| WO | WO-0122897 | 4/2001 |
| WO | WO-0170114 | 9/2001 |
| WO | WO03022167 | 3/2003 |
| WO | WO03082080 | 10/2003 |
| WO | WO-2005030072 | 4/2005 |
| WO | WO-2005041748 | 5/2005 |
| WO | WO-2005110528 | 11/2005 |
| WO | WO-2006041881 | 4/2006 |
| WO | WO2006086152 | 8/2006 |
| WO | WO2006105121 | 10/2006 |
| WO | WO-2007008954 | 1/2007 |
| WO | WO2007078997 | 7/2007 |
| WO | WO2008049084 | 4/2008 |
| WO | WO2009086007 | 7/2009 |
| WO | WO2011139589 | 11/2011 |
| WO | WO-2012019156 | 2/2012 |
| WO | WO2012054906 | 4/2012 |
| WO | WO-2013134548 | 9/2013 |

OTHER PUBLICATIONS

Barbieri, R. et al., "Treatment of polycystic ovary syndrome in adults," Wolters Kluwer Health, 2012, 11 pgs. <http://www.uptodate.com>.

Barria A. et al., "Ovarian Steroidal Response to Gonadotropins and β-Adrenergic Stimulation is Enhanced in Polycystic Ovary Syndrome: Role of Sympathetic Innervation." Endocrinology, 1993, vol. 133, No. 6, 8 pages.

Diamanti-Kandarakis, E. et al., "The Role of Genes and Environment in the Etiology of PCOS," Endocrine, vol. 30, No. 1, Aug. 2006, pp. 19-26.

Ehrmann, David, "Polycystic Ovary Syndrome," The New England Journal of Medicine, vol. 352, 2005, 1223-36.

Esler M. et al., "Catheter-Based Renal Denervation Reduces Total Body and Renal Noradrenaline Spillover and Blood Pressure in Resistant," Hypertension, J Hypertens vol. 27, 2009, 1 page.

Fauser et al. "Consensus on women's health aspects of polycystic ovary syndrome (PCOS): the Amsterdam ESHRE/ASRM-Sponsored 3rd PCOS Consensus Workshop Group." Fertility and sterility 2012; 97: 36 pages.

Hendriks et al. "Why does ovarian surgery in PCOS help? Insight into the endocrine implications of ovarian surgery for ovulation induction in polycystic overy syndrome." Human reproduction update, 2007; 13: 16 pages.

Himelein et al. "Polycystic ovary syndrome and mental health: A review." Obstet Gynecol. Surv. 2006; 61(11): 723-732.

Lansdown et al. "The Sympathetic Nervous System in Polycystic Ovary Syndrome: a novel therapeutic target?" Clinical endocrinology, 2012, 28 pages.

Lara et al., "Activation of ovarian sympathetic nerves in polycystic ovary syndrome." Endocrinology 1993; 133, 6 pages.

Lembo et al., "A lesson from polycystic ovarian syndrome: untangling the role of renal sympathetic nervous system on hypertension and insulin resistance." J Hypertens, 2011; 29: 2 pages.

Nakamura Y., "Treatment of Polycystic Ovary Syndrome: An Overview." Hormone Research 1990; 33: 1 page.

Schlaich MP et al., "A Novel Catheter Based Approach to Denervate the Human Kidney Reduces Blood Pressure and Muscle Sympathetic Nerve Activity in a Patient with the End Stage Renal Disease and Hypertension." J Hypertens 2009; 27: 1 page.

Schlaich MP et al., Renal sympathetic-nerve ablation for uncontrolled hypertension. N Engl J Med 2009; 361: 932-4.

Stener-Victorin et al. "Low-frequency electroacupuncture and physical exercise decrease high muscle sympathetic nerve activity in polycystic ovary syndrome," Am J Physiol Regul Integr Comp Physiol, 2009; 297: R387-95.

Allen, E.V., Sympathectomy for essential hypertension, Circulation, 1952, 6:131-140.

Bello-Reuss, E. et al., "Effects of Acute Unilateral Renal Denervation in the Rat," Journal of Clinical Investigation, vol. 56, Jul. 1975, pp. 208-217.

Bello-Reuss, E. et al., "Effects of Renal Sympathetic Nerve Stimulation on Proximal Water and Sodium Reabsorption," Journal of Clinical Investigation, vol. 57, Apr. 1976, pp. 1104-1107.

Bhandari, A. and Ellias, M., "Loin Pain Hematuria Syndrome: Pain Control with RFA to the Splanchanic Plexus," The Pain Clinc, 2000, vol. 12, No. 4, pp. 323-327.

(56) References Cited

OTHER PUBLICATIONS

Curtis, John J. et al., "Surgical Therapy for Persistent Hypertension After Renal Transplantation" Transplantation, 31:125-128 (1981).
Dibona, Gerald F. et al., "Neural Control of Renal Function," Physiological Reviews, vol. 77, No. 1, Jan. 1997, The American Physiological Society 1997, pp. 75-197.
Dibona, Gerald F., "Neural Control of the Kidney—Past, Present and Future," Nov. 4, 2002, Novartis Lecture, Hypertension 2003, 41 part 2, 2002 American Heart Association, Inc., pp. 621-624.
Janssen, Ben J.A. et al., "Effects of Complete Renal Denervation and Selective Afferent Renal Denervation on the Hypertension Induced by Intrarenal Norepinephrine Infusion in Conscious Rats", Journal of Hypertension 1989, 7: 447-455.
Katholi, Richard E., "Renal Nerves in the Pathogenesis of Hypertension in Experimental Animals and Humans," Am J. Physiol. vol. 245, 1983, the American Physiological Society 1983, pp. F1-F14.
Krum, Henry et al., "Catheter-Based Renal Sympathetic Denervation for Resistant Hypertension: A Multicentre Safety and Proof-of Principle Cohort Study," Lancet 2009; 373:1275-81.
Krum, et al., "Renal Sympathetic-Nerve Ablation for Uncontrolled Hypertension," New England Journal of Med. Aug. 2003, 361: 9, 3 pages.
Luippold, Gerd et al., "Chronic Renal Denervation Prevents Glomerular Hyperfiltration in Diabetic Rats", Nephrol Dial Transplant, vol. 19, No. 2, 2004, pp. 342-347.
Mahfoud et al. "Treatment strategies for resistant arterial hypertension" Dtsch Arztebl Int. 2011;108:725-731.
Osborn, et al., "Effect of Renal Nerve Stimulation on Renal Blood Flow Autoregulation and Antinatriuresis During Reductions in Renal Perfusion Pressure," Proceedings of the Society for Experimental Biology and Medicine, vol. 168, 77-81, 1981.
Page, I.H. et al., "The Effect of Renal Denervation on Patients Suffering From Nephritis," Feb. 27, 1935;443-458.
Page, I.H. et al., "The Effect of Renal Denervation on the Level of Arterial Blood Pressure and Renal Function in Essential Hypertension," J. Clin Invest. 1934;14:27-30.
Rocha-Singh, "Catheter-Based Sympathetic Renal Denervation," Endovascular Today, Aug. 2009, 4 pages.
Schlaich, M.P. et al., "Renal Denervation as a Therapeutic Approach for Hypertension: Novel Implications for an Old Concept," Hypertension, 2009; 54:1195-1201.
Schlaich, M.P. et al., "Renal Sympathetic-Nerve Ablation for Uncontrolled Hypertension," N Engl J Med 2009: 361(9): 932-934.
Smithwick, R.H. et al., "Splanchnicectomy for Essential Hypertension," Journal Am Med Assn. 1953; 152:1501-1504.
Symplicity HTN-1 Investigators; Krum H, Barman N, Schlaich M, et al. Catheter-based renal sympathetic denervation for resistant hypertension: durability of blood pressure reduction out to 24 months. Hypertension. 2011;57(5):911-917.
Symplicity HTN-2 Investigators, "Renal Sympathetic Denervation in Patients with Treatment-Resistant Hypertension (The Symplicity HTN-2 Trial): A Randomised Controlled Trial"; Lancet, Dec. 4, 2010, vol. 376, pp. 1903-1909.
United States Renal Data System, USRDS 2003 Annual Data Report: Atlas of End-Stage Renal Disease in the United States, National Institutes of Health, National Institute of Diabetes and Digestive and Kidney Diseases, 2003, 593 pages.
Valente, John F. et al., "Laparoscopic Renal Denervation for Intractable ADPKD-Related Pain", Nephrol Dial Transplant (2001) 16: 1 page.
Wagner, C.D. et al., "Very Low Frequency Oscillations in Arterial Blood Pressure After Autonomic Blockade in Conscious Dogs," Feb. 5, 1997, Am J Physiol Regul Integr Comp Physiol 1997, vol. 272, 1997 the American Physiological Society, pp. 2034-2039.
Ahmed, Humera et al., Renal Sympathetic Denervation Using an Irrigated Radiofrequency Ablation Catheter for the Management of Drug-Resistant Hypertension, JACC Cardiovascular Interventions, vol. 5, No. 7, 2012, pp. 758-765.
Avitall et al., "The creation of linear contiguous lesions in the atria with an expandable loop catheter,"Journal of the American College of Cardiology, 1999; 33; pp. 972-984.
Beale et al., "Minimally Invasive Treatment for Varicose Veins: A Review of Endovenous Laser Treatment and Radiofrequency Ablation", Lower Extremity Wounds 3(4), 2004, 10 pages.
Blessing, Erwin et al., Cardiac Ablation and Renal Denervation Systems Have Distinct Purposes and Different Technical Requirements, JACC Cardiovascular Interventions, vol. 6, No. 3, 2013, 1 page.
ClinicalTrials.gov, Renal Denervation in Patients with uncontrolled Hypertension in Chinese (2011), 6pages. www.clinicaltrials.gov/ct2/show/NCT01390831.
Excerpt of Operator's Manual of Boston Scientific's EPT-1000 XP Cardiac Ablation Controller & Accessories, Version of Apr. 2003, (6 pages).
Excerpt of Operator's Manual of Boston Scientific's Maestro 30000 Cardiac Ablation System, Version of Oct. 17, 2005 , (4 pages).
Holmes et al., Pulmonary Vein Stenosis Complicating Ablation for Atrial Fibrillation: Clinical Spectrum and Interventional Considerations, JACC: Cardiovascular Interventions, 2: 4, 2009, 10 pages.
Kandarpa, Krishna et al., "Handbook of Interventional Radiologic Procedures", Third Edition, pp. 194-210 (2002).
Mount Sinai School of Medicine clinical trial for Impact of Renal Sympathetic Denervation of Chronic Hypertension, Mar. 2013, 11 pages, http://clinicaltrials.gov/ct2/show/NCT01628198.
Opposition to European Patent No. EP1802370, Granted Jan. 5, 2011, Date of Opposition Oct. 5, 2011, 20 pages.
Opposition to European Patent No. EP2037840, Granted Dec. 7, 2011, Date of Opposition Sep. 7, 2012, 25 pages.
Opposition to European Patent No. EP2092957, Granted Jan. 5, 2011, Date of Opposition Oct. 5, 2011, 26 pages.
Oz, Mehmet, Pressure Relief, Time, Jan. 9, 2012, 2 pages. <www.time.com/time/printout/0,8816,2103278,00.html>.
Papademetriou, Vasillos, Renal Sympathetic Denervation for the Treatment of Difficult-to-Control or Resistant Hypertension, Int. Journal of Hypertension, 2011, 8 pages.
Prochnau, Dirk et al., Catheter-based renal denervation for drug-resistant hypertension by using a standard electrophysiology catheter; Euro Intervention 2012, vol. 7, pp. 1077-1080.
Purerfellner, Helmut et al., Incidence, Management, and Outcoma in Significant Pulmonary Vein Stenosis Complicating Ablation for Atrial Fibrillation, Am. J. Cardiol , 93, Jun. 1, 2004, 4 pages.
Purerfellner, Helmut et al., Pulmonary Vein Stenosis Following Catheter Ablation of Atrial Fibrillation, Curr. Opin Cardio. 20 :464-490, 2005.
Schneider, Peter A., "Endovascular Skills—Guidewire and Catheter Skills for Endovascular Surgery." Second Edition Revised and Expanded, 10 pages. (2003).
ThermoCool Irrigated Catheter and Integrated Ablation System, Biosense Webster (2006), 6 pages.
Tsao, Hsuan-Ming, Evaluation of Pulmonary Vein Stenosis after Catheter Ablation of Atrial Fibrillation, Cardiac Electrophysiology Review, 6, 2002, 4 pages.
Wittkampf et al., "Control of radiofrequency lesion size by power regulation," Journal of the American Heart Associate, 1989, 80: pp. 962-968.
Zheng et al., "Comparison of the temperature profile and pathological effect at unipolar, bipolar and phased radiofrequency current configurations," Journal of Interventional Cardiac Electrophysiology, 2001, pp. 401-410.
International Search Report and Written Opinion for International App. No. PCT/US13/29690, dated May 9, 2013, 10 pages.
Schlaich et al., Renal denervation: a potential new treatment modality for polycystic ovary syndrome? Journal of Hypertension. May 2011, vol. 29, Issue 5, p. 991-996.
Sverrisdottir et al., "Is Polycystic Ovary Syndrome Associated with High Sympathetic Nerve Activity and Size and Birth?" American Journal of Physiology—Endocrinology and Metabolism. Jan. 15, 2008, vol. 294, p. E576-E581, ISSN: 0193-1849. Fig. 1; p. E577, paragraph 14.
European Search Report for European Application No. 13159256, dated Oct. 17, 2013, 6 pages.

(56) References Cited

OTHER PUBLICATIONS

U.S. Appl. No. 95/002,110, filed Aug. 29, 2012, Demarais et al.
U.S. Appl. No. 95/002,209, filed Sep. 13, 2012, Levin et al.
U.S. Appl. No. 95/002,233, filed Sep. 13, 2012, Levin et al.
U.S. Appl. No. 95/002,243, filed Sep. 13, 2012, Levin et al.
U.S. Appl. No. 95/002,253, filed Sep. 13, 2012, Demarais et al.
U.S. Appl. No. 95/002,256, filed Sep. 13, 2012, Demarais et al.
U.S. Appl. No. 95/002,292, filed Sep. 14, 2012, Demarais et al.
U.S. Appl. No. 95/002,327, filed Sep. 14, 2012, Demarais et al.
U.S. Appl. No. 95/002,335, filed Sep. 14, 2012, Demarais et al.
U.S. Appl. No. 95/002,336, filed Sep. 14, 2012, Levin et al.
U.S. Appl. No. 95/002,356, filed Sep. 14, 2012, Demarais et al.
"2011 Edison Award Winners." Edison Awards: Honoring Innovations & Innovators, 2011, 6 pages, <http://www.edisonawards.com/BestNewProduct_2011.php>.
"2012 top 10 advances in heart disease and stroke research: American Heart Association/America Stroke Association Top 10 Research Report." American Heart Association, Dec. 17, 2012, 5 pages, <http://newsroom.heart.org/news/2012-top-10-advances-in-heart-241901>.
"Ardian(R) Receives 2010 EuroPCR innovation Award and Demonstrates Further Durability of Renal Denervation Treatment for Hypertension." PR Newswire, Jun. 3, 2010, 2 pages, <http://www.prnewswire.com/news-releases/ardianr-receives-2010-europcr-innovation-award-and-demonstrates-further-durability-of-renal-denervation-treatment-for-hypertension-95545014.html>.
"Boston Scientific to Acquire Vessix Vascular, Inc.: Company to Strengthen Hypertension Program with Acquisition of Renal Denervation Technology." Boston Scientific: Advancing science for life-Investor Relations, Nov. 8, 2012, 2 pages, <http://phx.corporate-ir.net/phoenix.zhtml?c=62272&p=irol-newsArticle&id=1756108>.
"Cleveland Clinic Unveils Top 10 Medical Innovations for 2012: Experts Predict Ten Emerging Technologies that will Shape Health Care Next Year." Cleveland Clinic, Oct. 6, 2011, 2 pages. <http://my.clevelandclinic.org/media_relations/library/2011/2011-10-6-cleveland-clinic-unveils-top-10-medical-innovations-for-2012.aspx>.
"Does renal denervation represent a new treatment option for resistant hypertension?" Interventional News, Aug. 3, 2010, 2 pages. <http://www.cxvascular.com/in-latest-news/interventional-news--latest-news/does-renal-denervation-represent-a-new-treatment-option-for-resistant-hypertension>.
"Iberis—Renal Sympathetic Denervation System: Turning innovation into quality care." [Brochure]. Terumo Europe N.V., 2013, Europe, 3 pages.
"Neurotech Reports Announces Winners of Gold Electrode Awards." Neurotech business report, 2009, 1 page. <http://www.neurotechreports.com/pages/goldelectrodes09.html>.
"Quick, Consistent, Controlled OneShot renal Denervation System" [Brochure], Covidien: positive results for life, 2013, (n.l.). 4 pages.
"Renal Denervation Technology of Vessix Vascular, Inc. been acquired by Boston Scientific Corporation (BSX) to pay up to $425 Million." Vessix Vascular Pharmaceutical Intelligence: A blog specializing in Pharmaceutical Intelligence and Analytics, Nov. 8, 2012, 21 pages, <http://pharmaceuticalintelligence.com/tag/vessix-vascular/>.
"The Edison Awards™" Edison Awards: Honoring Innovations & Innovators, 2013, 2 pages, <http://www.edisonawards.com/Awards.php>.
"The Future of Renal denervation for the Treatment of Resistant Hypertension." St. Jude Medical, Inc., 2012, 12 pages.
"Vessix Renal Denervation System: So Advanced It's Simple," [Brochure], Boston Scientific: Advancing science for life, 2013, 6 pages.
Asbell, Penny, "Conductive Keratoplasty For The Correction of Hyperopia." Tr Am Ophth Soc. 2001, vol. 99, 10 pages.
Badoer, Emilio, "Cardiac afferents play the dominant role in renal nerve inhibition elicited by volume expansion in the rabbit." Am J Physiol Regul Integr Comp Physiol, vol. 274, 1998, 7 pages.
Bengel, Frank, "Serial Assessment of Sympathetic Reinnervation After Orthotopic Heart Transplantation: A longitudinal Study Using PET and C-11 Hydroxyephedrine." Circulation, vol. 99, 1999, 7 pages.
Benito, F., et al. "Radiofrequency catheter ablation of accessory pathways in infants." Heart, 78:160-162 (1997).
Bettmann, Michael, Carotid Stenting and Angioplasty: A Statement for Healthcare Professionals From the Councils on Cardiovascular Radiology, Stroke, Cardio-Thoracic and Vascular Surgery, Epidemiology and Prevention, and Clinical Cardiology, American Heart Association, Circulation, vol. 97, 1998, 4 pages.
Bohm, Michael et al., "Rationale and design of a large registry on renal denervation: the Global Symplicity registry" EuroIntervention. vol. 9, 2013, 9 pages.
Brosky, John, "EuroPCR 2013: CE-approved devices line up for renal denervation approval." Medical Device Daily, May 28, 2013, 3 pages, <http://www.medicaldevicedaily.com/servlet/com accumedia.web.Dispatcher?next=bioWorldHeadlines_article&forceid=83002>.
Davis, Mark et al., "Effectiveness of Renal Denervation Therapy for Resistant Hypertension," Journal of the American College of Cardiology, vol. 62, No. 3, 2013, 11 pages.
Dibona, G.F. "Sympathetic nervous system and kidney in hypertension." Nephrol and Hypertension, 11: 197-200 (2002).
Dubuc, M., et al., "Feasibility of cardiac cryoablation using a transvenous steerable electrode catheter," J Interv Cardiac Electrophysiol, 2:285-292 (1998).
Final Office Action; U.S. Appl. No. 12/827,700; dated Feb. 5, 2013, 61 pages.
Geisler, Benhamin et al., "Cost-Effectiveness and Clinical Effectiveness of Catheter-Based Renal Denervation for Resistant Hypertension." Journal of the American College of Cardiology, col. 60, No. 14, 2012, 7 pages.
Gelfand, M., et al., "Treatment of renal failure and hypertension." U.S. Appl. No. 60/442,970, Jan. 29, 2003, 23 pages.
Gertner, Jon, "Meet The Tech Duo That's Revitalizing The Medical Device Industry." Fast Company, Apr. 15, 2013, 6:00 AM, 17 pages, <http://www.fastcompany.com/3007845/meet-tech-duo-thats-revitalizing-medical-device-industry>.
Golwyn, D. H., Jr., et al. "Percutaneous Transcatheter Renal Ablation with Absolute Ethanol for Uncontrolled Hypertension or Nephrotic Syndrome: Results in 11 Patients with End-Stage Renal Disease." JVIR. 8: 527-533 (1997).
Hall, W. H., et al. "Combined embolization and percutaneous radiofrequency ablation of a solid renal tumor." Am. J. Roentgenol,174: 1592-1594 (2000).
Han, Y.-M, et al., "Renal artery ebolization with diluted hot contrast medium: An experimental study." J Vasc Interv Radiol. 12: 862-868 (2001).
Hansen, J. M., et al. "The transplanted human kidney does not achieve functional reinnervation." Clin. Sci. 87: 13-19 (1994).
Hendee, W. R. et al. "Use of Animals in Biomedical Research: The Challenge and Response." *American Medical Association White Paper* (1988) 39 pages.
Hering, Dagmara et al., "Chronic kidney disease: role of sympathetic nervous system activation and potential benefits of renal denervation." EuroIntervention, vol. 9, 2013, 9 pages.
Huang et al., "Renal denervation prevents and reverses hyperinsullnemia-induced hypertension in rats." Hypertension 32 (1998) pp. 249-254.
Imimdtanz, "Medtronic awarded industry's highest honor for renal denervation system." The official blog of Medtronic Australasia, Nov. 12, 2012, 2 pages, <http://97waterlooroad.wordpress.com/2012/11/12/medtronic-awarded-industrys-highest-honour-for-renal-denervation-system/>.
Kaiser, Chris, AHA Lists Year's Big Advances in CV Research, medpage Today, Dec. 18, 2012, 4 pages, <http://www.medpagetoday.com/Cardiology/PCI/36509>.
Kompanowska, E., et al., "Early Effects of renal denervation in the anaesthetised rat: Natriuresis and increased cortical blood flow," J Physiol, 531. 2:527-534 (2001).
Lee, S.J., et al., "Ultrasonic energy in endoscopic surgery." Yonsei Med J, 40:545-549 (1999).

(56) References Cited

OTHER PUBLICATIONS

Linz, Dominik et al., "Renal denervation suppresses ventricular arrhythmias during acute ventricular ischemia in pigs," Heart Rhythm, vol. 0, No. 0, 2013, 6 pages.
Lustgarten, D.L.,et al., "Cryothermal ablation: Mechanism of tissue injury and current experience in the treatment of tacharrhythmias." Progr Cardiovasc Dis, 41:481-498 (1999).
Mabin, Tom et al., "First experience with endovascular ultrasound renal denervation for the treatment of resistant hypertension." EuroIntervention, vol. 8, 2012. 5 pages.
Mahfoud, Felix et al., "Ambulatory Blood Pressure Changes after Renal Sympathetic Denervation in Patients with Resistant Hypertension." Circulation. 2013, 25 pages.
Mahfoud, Felix et al., "Expert consensus document from the European Society of Cardiology on catheter-based renal denervation." European Heart Journal, 2013, 9 pages.
Mahfoud, Felix et al., "Renal Hemodynamics and Renal Functional After Catheter-Based Renal Sympathetic Denervation in Patients With Resistant Hypertension." Hypertension, 2012, 6 pages.
Medical-Dictionary.com, Definition of "Animal Model," http://medical-dictionary.com (search "Animal Model"), 2005, 1 page.
Medtronic, Inc., Annual Report (Form 10-K) (Jun. 28, 2011) 44 pages.
Millard, F. C., et al, "Renal Embolization for ablation of function in renal failure and hypertension," Postgraduate Medical Journal, 65, 729-734, (1989).
Oliveira, V., et al., "Renal denervation normalizes pressure and baroreceptor reflex in high renin hypertension in conscious rats." Hypertension, 19:II-17-II-21 (1992).
Ong, K. L., et al. "Prevaience, Awareness, Treatment, and Control of Hypertension Among United States Adults 1999-2004." Hypertension, 49: 69-75 (2007) (originally published online Dec. 11, 2006).
Ormiston, John et al., "First-in-human use of the OneShot™ renal denervation system from Covidien." EuroIntervention. vol. 8, 2013, 4 pages.
Ormiston, John et al., "Renal denervation for resistant hypertension using an irrigated radiofrequency balloon: 12-month results from the Renal Hypertension Ablation System (RHAS) trial." EuroIntervention, vol. 9. 2013, 5 pages.
Pedersen, Amanda, "TCT 2012: Renal denervation device makers play show and tell." Medical Device Dally, Oct. 26, 2012, 2 pages, <http://www.medicaldevicedaily.com/servlet/com.accumedia.web.Dispatcher?next=bioWorldHeadlines_article&forceid=80880>.
Peet, M., "Hypertension and Its Surgical Treatment by bilateral supradiaphragmatic splanchnicectomy" Am J Surgery (1948) pp. 48-68.
Renal Denervation (RDN), Symplicity RDN System Common Q&A (2011), 4 pages, http://www.medtronic.com/rdn/mediakit/RDN%20FAQ.pdf.
Schauerte, P., et al. "Catheter ablation of cardiac autonomic nerves for prevention of vagal atrial fibrillation," Circulation, 102:2774-2780 (2000).
Schlaich, Markus et al., "Renal Denervation in Human Hypertension: Mechanisms, Current Findings, and Future Prospects." Curr Hypertens Rep, vol. 14, 2012. 7 pages.
Schmid, Axel et al., "Does Renal Artery Supply Indicate Treatment Success of Renal Denervation." Cardiovasc Intervent Radiol. vol. 36. 2013, 5 pages.
Schmieder, Roland E. et al., "Updated ESH position paper on interventional therapy of resistant hypertension," EuroIntervention, vol. 9, 2013, 9 pages.
Sievert, Horst, "Novelty Award EuroPCR 2010." PCR, 2010, 15 pages.
Solis-Herruzo et al., "Effects of lumbar sympathetic block on kidney function in cirrhotic patients with hepatorenal syndrome," J. Hepatol. 5 (1987), pp. 167-173.
Stella, A., et al., "Effects of reversible renal denervation on haemodynamic and excretory functions on the ipsilateral and contraleteral kidney in the cat" Hypertension, 4:181-188 (1986).
Stouffer, G. A. et al., "Catheter-based renal denervation in the treatment of resistent hypertension." Journal of Molecular and Cellular Cardiology, vol. 62, 2013, 6 pages.
Swartz, J.F., et al., "Radiofrequency endocardial catheter ablation of accessory atrioventricular pathway atrial insertion sites," Circulation, 87: 487-499 (1993).
Uchida, F., et al., "Effect of radiofrequency catheter ablation on parasympathetic denervation: A comparison of three different ablation sites." PACE, 21:2517-2521 (1998).
Verloop, W. L. et al., "Renal denervation: a new treatment option in resistant arterial hypertension." Neth Heart J., Nov. 30, 2012, 6 pages, <http://www.ncbi.nlm.nih.gov/pmc/articles/PMC3547427/>.
Weinstock, M., et al., "Renal denervation prevents sodium retention and hypertension in salt sensitive rabbits with genetic baroreflex impairment." Clinical Science, 90:287-293 (1996).
Wilcox, Josiah N., Scientific Basis Behind Renal Denervation for the Control of Hypertension, ICI 2012, Dec. 5-6, 2012. 38 pages.
Worthley, Stephen et al., "Safety and efficacy of a multi-electrode renal sympathetic denervation system in resistant hypertension: the EnligHTN I trial." European Heart Journal, vol. 34, 2013, 9 pages.
Worthley, Stephen, "The St. Jude Renal Denervation System Technology and Clinical Review." The University of Adelaide Australia, 2012, 24 pages.
Zuern, Christine S., "Impaired Cardiac Baroflex Sensitivity Predicts Response to Renal Sympathetic Denervation in Patients with Resistant Hypertension." Journal of the American College of Cardiology, 2013, doi: 10.1016/j.jacc.2013.07.046. 24 pages.
Miller, Reed, "Finding A Future For Renal Denervation With Better Controlled Trials" Pharma & Medtech Business Intelligence, Article #01141006003, Oct. 6, 2014, 4 pages.
Papademetriou, Vasilios, "Renal Denervation and Symplicity HTN-3: "Dubium Sapientiae Initium" (Doubt is the Beginning of Wisdom)", Circulation Research, 2014, 115: 211-214.
Papademetriou, Vasilios et al., "Renal Nerve Ablation for Resistant Hypertension: How Did We Get Here, Present Status, and Future Directions," Circulation. 2014: 129: 1440-1450.
Papademetriou, Vasilios et al., "Catheter-Based Renal Denervation for Resistant Hypertension: 12-Month Results of the EnligHTN I First-in-Human Study Using a Multielectrode Ablation System." Hypertension. 2014; 64: 565-572.
Doumas, Michael et al., "Renal Nerve Ablation for Resistant Hypertension: The Dust Has Not Yet Settled." The Journal of Clinical Hypertension, 2014; vol. 16, No. 6, 2 pages.
Messerli, Franz H et al. "Renal Denervaton for Resistant Hypertension: Dead or Alive?" Healio Cardiology today's Intervention, May/Jun. 2014, 2 pages.
Dodge, et al., "Lumen Diameter of Normal Human Coronary Arteries Influence of Age, Sex, Anatomic Variation, and Left Ventricular Hypertrophy or Dilation", Circulation, 1992, vol. 86 (1), 232-246 pp.
International Search Report and Written Opinion for International App. No. PCT/US2011/03349, Applicant Medtronic Ardian LLC, dated Nov. 22, 2011, 17 pgs.
International Search Report and Written Opinion for International App. No. PCT/US2011/057402, Applicant Medtronic Ardian Luxembourg S.A.R.L., dated Apr. 23, 2012, 19 pgs.
Opposition to European Patent No. 2465470, dated Oct. 28, 2015, Date of Opposition Jul. 27, 2016, 34 pp.
Pieper, et al., "Design and Implementation of a New Computerized System for Intraoperative Cardiac Mapping" Journal of Applied Physiology, 1991, vol. 71 (4), pp. 1529-1539.
Remo, et al., "Safety and Efficacy of Renal Denervation as a Novel Treatment of Ventricular Tachycardia Storm in Patients with Cardiomyopathy" Heart Rhythm, 2014, 11(4), pp. 541-546.
Schlaich, et al., Renal Denervation: a Potentional New Treatment Modality for Polycystic Ovary Syndrome?, Journal of Hypertension 2011, 29:991-996.
Stener-Victorin, et al., Acupuncture in Polycystic Ovary Syndrome: Current Experimental and Clinical Evidence, Journal of Neuroendocrinology, Mar. 2008, 20(3): 290-298.
Torres, et al., "Autosomal Dominant Polycystic Kidney Disease." The Lancet 2007; 369: 1287-1301.
U.S. Appl. No. 11/363,867, filed Feb. 27, 2006, 70 pp.

(56) References Cited

OTHER PUBLICATIONS

U.S. Appl. No. 60/813,589, filed Dec. 29, 2005, 62 pp.
U.S. Appl. No. 60/852,787, filed Oct. 18, 2006, 112 pp.
Ureter, https://en.wikipedia.org/wiki/Ureter, Jun. 2016, 6 pp.
Hendriks, et al., "Why Does Ovarian Surgery in PCOS Help? Insight into the Endocrine Implications of Ovarian Surgery of Ovulation Induction in Polycystic Ovary Syndrome", Human Reproduction Update, 2007, vol. 13 (3), pp. 249-264.
University of Michigan Medical School, Medical Gross Anatomy—Anatomy Tables—Nerves, The Material Presented in these Tables is Contained in the book: Med Charts Anatomy by Thomas R. Gest & Jaye Schlesinger, 1995.

\* cited by examiner

Arterial Vasculature

Venous Vasculature

OVARIAN NEUROMODULATION AND ASSOCIATED SYSTEMS AND METHODS

CROSS-REFERENCE TO RELATED APPLICATION(S)

The present application claims priority to U.S. Provisional Patent Application No. 61/608,452, filed Mar. 8, 2012, entitled "OVARIAN NEUROMODULATION AND ASSOCIATED SYSTEMS AND METHODS," which is incorporated herein in its entirety by reference.

TECHNICAL FIELD

The present technology relates generally to modulation of ovarian nerves and associated systems and methods.

BACKGROUND

Ovarian sympathetic neural activity can cause or exacerbate several ovarian conditions, including, but not limited to, polycystic ovary syndrome, infertility, and dysfunctional hormone or steroid production. Polycystic ovary syndrome (PCOS) is a common endocrine disorder affecting women of reproductive ages (e.g., 12-45 years old). Symptoms of PCOS can include oligoovulation or anovulation resulting in irregular menstruation, amenorrhea, ovulation-related infertility, and enlarged or polycystic ovaries. Other symptoms include excess of androgenic hormones (e.g., testosterone) which can result in acne and hirsutism. Clinical complications, such as insulin resistance, obesity, Type 2 diabetes, high cholesterol, and hypertension can also be common in PCOS patients. Further complications can include development of endometrial cancer or breast cancer. Most prescribed treatments address specific manifestations of PCOS and do not address underlying causes of the disease. Moreover, many of these treatments only address specific sequelae individual symptoms or indications) of the disease, and patients can be required to combine multiple treatment programs for treating these conditions and/or complications separately. For example, androgen excess and associated symptoms (e.g., hirsutism, acne) are commonly treated with estrogen-progestin contraceptives, antiandrogens, anti-acne treatments, and prescription drugs and over-the-counter depilatories for removing or slowing unwanted hair growth. Additionally, anovulation and fertility issues are treated with ovulation promoting drugs (e.g., clomiphene or follicle stimulating hormone (FSH) injections) or in vitro fertilization. Other treatments are prescribed for PCOS patients having hypertension (e.g., anti-hypertensive medications), hyperlipidemia (e.g., statins, other cholesterol lowering agents), and insulin resistance/Type 2 diabetes (e.g., metformin, other diabetic medications). Such pharmacologic strategies, however, have significant limitations including limited efficacy, side effects, long-term maintenance regimens and others.

The sympathetic nervous system (SNS) is a primarily involuntary bodily control system typically associated with stress responses. Fibers of the SNS extend through tissue in almost every organ system of the human body. For example, some fibers extend from the brain, intertwine along the aorta, and branch out to various organs. As groups of fibers approach specific organs, fibers particular to the organs can separate from the groups. Signals sent via these and other fibers can affect characteristics such as pupil diameter, gut motility, and urinary output. Such regulation can have adaptive utility in maintaining homeostasis or in preparing the body for rapid response to environmental factors. Chronic activation of the SNS, however, is a common maladaptive response that can drive the progression of many disease states. Excessive activation of the ovarian SNS has been identified experimentally and in humans as a likely contributor to the complex pathophysiology of PCOS. As examples, studies measuring efferent postganglionic muscle sympathetic nerve activity (MSNA) in PCOS patients revealed that PCOS is associated with high MSNA. Elevated testosterone and cholesterol lipid levels were identified as independent predictors of MSNA in PCOS. Involvement of the SNS in PCOS can be further characterized by finding that there is a greater density of catecholaminergic nerve fibers in polycystic ovaries and altered peripheral catecholamine secretion in adolescent PCOS patients. It is also known that activation of the sympathetic neurons innervating the ovary precedes the development of cystic ovaries in rats.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure.

DETAILED DESCRIPTION

Figure 1A:
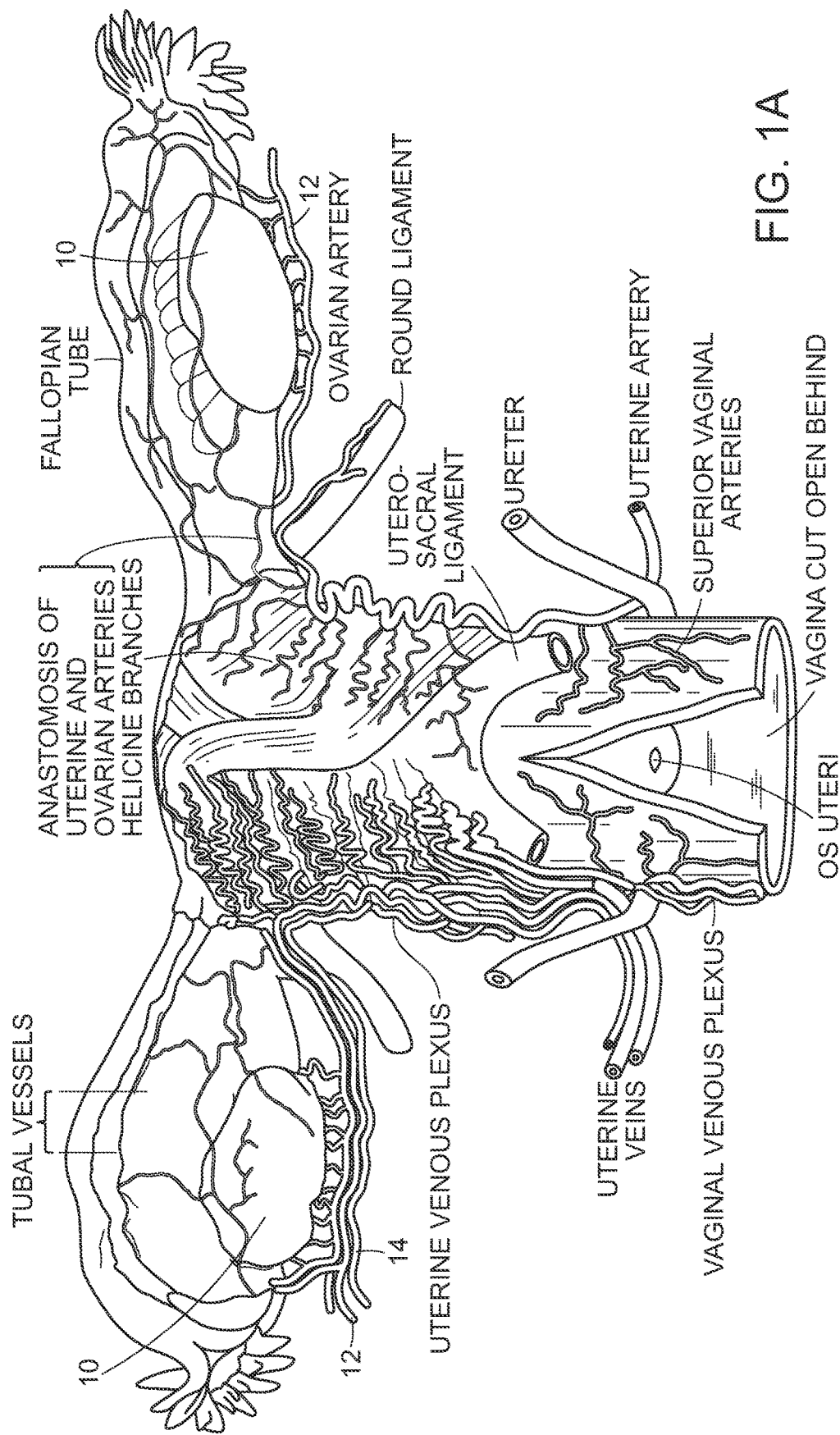
FIG. 1A is an anatomical view illustrating the ovarian artery and nearby organs and vessels.

The present technology is generally directed to modulation of ovarian nerves to treat at least one condition associated with ovarian sympathetic activity (e.g., overactivity or hyperactivity) and/or central sympathetic activity (e.g., overactivity or hyperactivity). For example, several embodiments are directed to modulation of ovarian nerves to treat polycystic ovary syndrome and related conditions, such as infertility and dysfunctional hormone or steroid production. As discussed in greater detail below, ovarian neuromodulation can include rendering neural fibers inert, inactive, or otherwise completely or partially reduced in function. This result can be electrically-induced, thermally-induced, or induced by another mechanism during an ovarian neuromodulation procedure, e.g., a procedure including percutaneous transluminal intravascular access.

Specific details of several embodiments of the technology are described below with reference to FIGS. 1A-8F. The embodiments can include, for example, modulating nerves proximate (e.g., at or near) an ovarian artery, an ovarian vein, and/or other suitable structures. Although many of the embodiments are described herein with respect to electrically-induced, thermally-induced, and chemically-induced approaches, other treatment modalities in addition to those described herein are within the scope of the present technology. Additionally, other embodiments of the present technology can have different configurations, components, or procedures than those described herein. A person of ordinary skill in the art, therefore, will accordingly understand that the technology can have other embodiments with additional elements and that the technology can have other embodiments without several of the features shown and described below with reference to FIGS. 1A-8F.

As used herein, the terms "distal" and "proximal" define a position or direction with respect to the treating clinician or clinician's control device (e.g., a handle assembly). "Distal" or "distally" can refer to a position distant from or in a direction away from the clinician or clinician's control device. "Proximal" and "proximally" can refer to a position near or in a direction toward the clinician or clinician's control device.

I. POLYCYSTIC OVARY SYNDROME

PCOS is a common endocrine abnormality in women and can be characterized by androgen excess, hyperinsulinemia, and/or other physiological conditions. The etiology of PCOS is uncertain; however evidence suggests that it results from both genetic susceptibility as well as environmental influences including the presence of obesity. The clinical presentation of PCOS can include reproductive (e.g., oligo/amenorrhea, infertility, and hirsutism), metabolic (e.g., obesity, metabolic syndrome, insulin resistance, increased cardiovascular risk profile), and psychological (e.g., depression, anxiety, body dissatisfaction and eating disorders, diminished sexual satisfaction, etc.) features. Experimentally, PCOS has been shown to correlate with a localized increase in ovarian sympathetic nerve activity (Lara et al., 1993, Endocrinology 133: 2690-2695; incorporated herein by reference in its entirety) and global increase in sympathetic nervous system tone such as MSNA (Sverrisdottir et al., 2008, Am J Physiol Endocrinol Metab 294: E576-581; incorporated herein by reference in its entirety). Additionally, the degree of sympathoexcitation may be related to the degree of PCOS severity.

Sympathetic nerves can contribute to cardiovascular, metabolic, and/or other features that characterize PCOS. For example, among other PCOS presentations, obesity and hypertension can be characterized by increased efferent sympathetic drive to the kidneys and increased systemic sympathetic nerve firing modulated by afferent signaling from renal sensory nerves. The role of renal sympathetic nerves as contributors to the pathogenesis of elevated blood pressure, particularly in obese patients, has been demonstrated both experimentally and in humans. Apart from its role in cardiovascular regulation, sympathetic nervous system activation also has metabolic effects resulting in increased lipolysis and increased levels of fatty acids in plasma, increased hepatic gluconeogenesis, and alterations in pancreatic insulin release. Chronic sympathetic activation predisposes to the development of insulin resistance, which is often associated with obesity and hypertension and can be a key feature of PCOS.

A patient suspected of having PCOS can be positively diagnosed if they present with the following criteria: (1) excess androgen activity, (2) oligoovulation/anovulation and/or polycystic ovaries (assessed, for example, by gynecologic ultrasound or pelvic laparoscopy), and (3) other entities are excluded that would cause excess androgen activity. Androgen excess can be tested by measuring total and free testosterone levels. Androstenedion androgen precursor) can also be measured as levels are typically elevated in female patients having PCOS. As examples, polycystic ovaries can be substantiated by a finding of twelve or more follicles measuring 2-9 mm in diameter, or by finding increased ovarian volume (>10 cm$^3$). Further tests for imbalances and/or irregularities in patients suspected of having or having been diagnosed with PCOS using the above criteria can include assessing levels of hormones (e.g., estrogen. FSH, LH, 17-ketosteriods), tasting glucose levels, lipid levels, prolactin levels, and thyroid function tests. In further embodiments, PCOS patients or patients suspected of having PCOS can be assessed fir elevated sympathetic nerve activity, including establishing measurements for markers of elevated sympathetic nerve activity, including for example, MSNA, total body plasma norepinephrine spillover levels, and heart rate variability.

II. OVARIAN NEUROMODULATION

Ovarian neuromodulation is the partial or complete incapacitation or other effective disruption or regulation of nerves innervating the ovaries, e.g., nerves terminating in or originating from an ovary or in structures closely associated with an ovary. In particular, ovarian neuromodulation comprises inhibiting, reducing, blocking, pacing, upregulating, and/or downregulating neural communication along neural fibers (e.g., efferent and/or afferent neural fibers) innervating the ovaries. Such incapacitation, disruption, and/or regulation can be long-term (e.g., permanent or for periods of months, years, or decades) or short-term (e.g., for periods of minutes, hours, days, or weeks). While long-term disruption of the ovarian nerves can be desirable for alleviating symptoms and other sequelae associated with PCOS over longer periods of time, short-term modulation of the ovarian nerves may also be desirable. For example, some patients may benefit from short-term modulation to address issues relating to fertility (e.g., to induce ovulation). Ovarian sympathetic neural activity can cause or exacerbate several ovarian conditions, including, but not limited to, polycystic ovary syndrome, infertility, and dysfunctional hormone or steroid production. Ovarian neuromodulation is expected to be useful in treating these conditions. Methods and systems for ovarian neuromodulation for efficaciously treating several clinical conditions characterized by increased ovarian sympathetic activity, such as PCOS and associated conditions, are described herein.

Furthermore, ovarian afferent sympathetic activity can contribute to central sympathetic tone or drive. Accordingly, ovarian neuromodulation is expected to be useful in treating clinical conditions associated with central sympathetic activity (e.g., overactivity or hyperactivity), particularly conditions associated with central sympathetic overstimulation. Conditions associated with central sympathetic activity (e.g., overactivity or hyperactivity) include, for example, hypertension, heart failure, acute myocardial infarction, metabolic syndrome, insulin resistance, diabetes, left ventricular hypertrophy, chronic and end stage renal disease, inappropriate fluid retention in heart failure, cardio-renal syndrome, polycystic kidney disease, osteoporosis, and sudden death, among other conditions.

By way of theory, targeting both afferent and efferent ovarian nerves (e.g., via a catheter-based approach, extracorporeal ultrasound) may cause beneficial effects extending well beyond the ovaries and other systemic sequelae of PCOS, such as increased cardiovascular risk. The role of sympathetic activation for blood pressure regulation is well established, as is the relevance of increased renal sympathetic nerve activity for the alterations in renal blood flow and glomerular filtration rate. There is now also clear evidence that sympathetic activation results in adverse consequences on metabolic control, including insulin sensitivity. Additionally, overactivity of the sympathetic nervous system is implicated in the specific etiology of PCOS. Some aspects of methods of treating PCOS patients using ovarian neuromodulation are at least in part derived from the recognition described herein that the ovaries may contribute to elevated central sympathetic drive.

While the ovarian nerves function to innervate the ovaries and connect the ovaries with the central nervous system, the ovarian nerves may be unnecessary for general health. Accordingly, in some patients, such as patients having PCOS, reducing ovarian sympathetic drive, central sympathetic drive, and/or achieving other benefits obtained from ovarian neuromodulation can outweigh the complete or partial loss of ovarian-nerve functionality.

Several properties of the ovarian vasculature may inform the design of treatment devices and associated methods for achieving ovarian neuromodulation, for example, via intravascular access, and impose specific design requirements for such devices. Specific design requirements may include accessing the ovarian artery, facilitating stable contact between the energy delivery elements of such devices and a luminal surface or wall of the ovarian artery, and/or effectively modulating the ovarian nerves with the neuromodulatory apparatus.

A. Selected Examples of Neuromodulation Modalities

Various techniques can be used to partially or completely incapacitate neural pathways, such as those innervating the ovary. Ovarian neuromodulation in accordance with embodiments of the present technology can be electrically-induced, thermally-induced, chemically-induced, or induced in another suitable manner or combination of manners at one or more suitable treatment locations during a treatment procedure. For example, the purposeful application of radio frequency (RF) energy (monopolar and/or bipolar), pulsed RF energy, microwave energy, optical energy, ultrasound energy (e.g., intravascularly delivered ultrasound, extracorporeal ultrasound, high-intensity focused ultrasound (HIFU)), cryotherapeutic energy, direct heat energy, radiation (e.g., infrared, visible, gamma), chemicals (e.g., drugs or other agents), or combinations thereof to tissue at a treatment location can induce one or more desired effects at the treatment location, e.g., broadly across the treatment location or at localized regions of the treatment location.

Figure 1B:
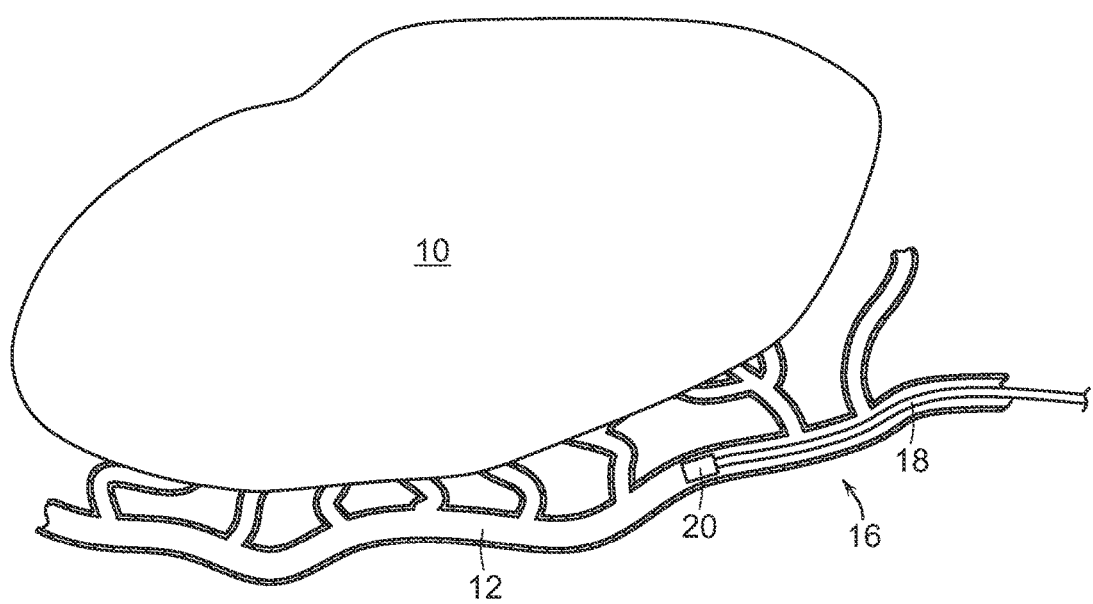
FIG. 1B is a partially cross-sectional view illustrating neuromodulation at a treatment location within the ovarian artery in accordance with an embodiment of the present technology.

FIG. 1A is an anatomical view illustrating the ovaries 10 and nearby organs and vessels, including an ovarian artery 12. Treatment procedures for ovarian neuromodulation in accordance with embodiments of the present technology can include applying a treatment modality at one or more treatment locations proximate a structure having a relatively high concentration of ovarian nerves. In some embodiments, for example, at least one treatment location can be proximate a portion of the ovarian artery 12, a branch of the ovarian artery 12, an ostium of the ovarian artery 12, an ovarian vein 14, a branch of an ovarian vein, an ostium of an ovarian vein, and/or another suitable structure (e.g., another suitable structure extending along the suspensory ligament) in the vicinity of ovarian nerves. FIG. 1B, for example, is a cross-sectional view illustrating neuromodulation at a treatment location within the ovarian artery 12. As shown in FIG. 1B, a treatment device 16 including a shaft 18 and a therapeutic element 20 can be extended toward the ovarian artery 12 to locate the therapeutic element 20 at the treatment location within the ovarian artery 12. The therapeutic element 20 can be configured for neuromodulation at the treatment location via a suitable treatment modality, e.g., cryotherapeutic, direct heat, electrode-based, transducer-based, chemical-based, or another suitable treatment modality.

The treatment location can be proximate (e.g., at or near) a vessel or chamber wall (e.g., a wall of an ovarian artery, an ovarian vein, and/or another suitable structure), and the treated tissue can include tissue proximate the treatment location. For example, with regard to the ovarian artery 12, a treatment procedure can include modulating nerves in the ovarian plexus, which lay at least partially within or adjacent to the adventitia of the ovarian artery. In some embodiments it may be desirable to modulate ovarian nerves from a treatment location within a vessel and in close proximity to an ovary, e.g., closer to the ovary 10 than to a trunk of the vessel. This can increase the likelihood of modulating nerves specific to the ovary, while decreasing the likelihood of modulating nerves that extend to other organs. Vessels can decrease in diameter and become more tortuous as they extend toward an ovary 10. Accordingly, modulating ovarian nerves from a treatment location in close proximity to an ovary can include using a device (e.g., treatment device 16) having size, flexibility, torque-ability, kink resistance, and/or other characteristics suitable for accessing narrow and/or tortuous portions of vessels.

In some embodiments, the purposeful application of energy (e.g., electrical energy, thermal energy, etc.) to tissue can induce one or more desired thermal heating and/or cooling effects on localized regions of the ovarian artery 12, for example, and adjacent regions along all or a portion of the ovarian plexus, which lay intimately within or adjacent to the adventitia of the ovarian artery (e.g., carried in the suspensory ligament of the ovary). Some embodiments of the present technology, for example, include cryotherapeutic ovarian neuromodulation, which can include cooling tissue at a target site in a manner that modulates neural function. The mechanisms of cryotherapeutic tissue damage include, for example, direct cell injury (e.g., necrosis), vascular injury (e.g., starving the cell from nutrients by damaging supplying blood vessels), and sublethal hypothermia with subsequent apoptosis. Exposure to cryotherapeutic cooling can cause acute cell death (e.g., immediately after exposure) and/or delayed cell death (e.g., during tissue thawing and subsequent hyperperfusion). Several embodiments of the present technology include cooling a structure at or near an inner surface of a vessel or chamber wall such that proximate (e.g., adjacent) tissue is effectively cooled to a depth where sympathetic (efferent and/or afferent) ovarian nerves reside. For example, a cooling structure can be cooled to the extent that it causes therapeutically-effective, cryogenic ovarian-nerve modulation. Sufficiently cooling at least a portion of a sympathetic ovarian nerve may slow or potentially block conduction of neural signals to produce a prolonged or permanent reduction in ovarian sympathetic activity. In some embodiments, a cryotherapeutic treatment modality can include cooling that is not configured to cause neuromodulation. For example, the cooling can be at or above cryogenic temperatures and can be used to control neuromodulation via another treatment modality, e.g., to reduce damage to non-targeted tissue when targeted tissue adjacent to the non-targeted tissue is heated.

Cryotherapeutic treatment can be beneficial in certain embodiments. For example, rapidly cooling tissue can provide an analgesic effect such that cryotherapeutic treatment can be less painful than other treatment modalities. Neuromodulation using cryotherapeutic treatment can therefore require less analgesic medication to maintain patient comfort during treatment procedure compared to neuromodulation using other treatment modalities. Additionally, reducing pain can reduce patient movement and thereby increase operator success and/or reduce procedural complications. Cryogenic cooling also typically does not cause significant collagen tightening, and therefore is not typically associated with vessel stenosis. In some embodiments, cryotherapeutic treatment can include cooling at temperatures that can cause therapeutic elements to adhere to moist tissue. This can be beneficial because it can promote stable, consistent, and continued contact during treatment. The typical conditions of treatment can make this an attractive feature because, for example, patients can move during treatment, catheters associated with therapeutic elements can move, and/or respiration can cause the ovaries to rise and fall and thereby move the ovarian vasculature. In addition, blood flow is pulsatile and can cause structures associated with the ovaries to pulse. Cryogenic adhesion also can facilitate intravascular positioning, particularly in relatively small structures (e.g., relatively short arteries) in which stable intravascular positioning can be difficult to achieve.

As an alternative to or in conjunction with cryotherapeutic cooling, other suitable energy delivery techniques, such as electrode-based or transducer-based approaches, can be used for therapeutically-effective ovarian neuromodulation. Electrode-based or transducer-based treatment can include delivering electrical energy and/or another form of energy to tissue and/or heating tissue at a treatment location in a manner that modulates neural function. For example, sufficiently stimulating and/or heating at least a portion of a sympathetic ovarian nerve can slow or potentially block conduction of neural signals to produce a prolonged or permanent reduction in sympathetic activity. As noted previously, suitable energy modalities can include, for example, RF energy (monopolar and/or bipolar), pulsed RF energy, microwave energy, ultrasound energy (e.g., intravascularly delivered ultrasound, extracorporeal ultrasound. HIFU), laser energy, optical energy, magnetic energy, direct heat, or other suitable energy modalities alone or in combination. Where a system uses a monopolar configuration, a return electrode or ground patch fixed externally on the subject can be used. Moreover, electrodes (or other energy delivery elements) can be used alone or with other electrodes in a multi-electrode array. Examples of suitable multi-electrode devices are described in U.S. patent application Ser. No. 13/281,360, filed Oct. 25, 2011, and incorporated herein by reference in its entirety. Other suitable devices and technologies, such as cryotherapeutic devices, are described in U.S. patent application Ser. No. 13/279,330, filed Oct. 23, 2011, and additional thermal devices are described in U.S. patent application Ser. No. 13/279,205, filed Oct. 21, 2011, each of which are incorporated herein by reference in their entireties.

Thermal effects can include both thermal ablation and non-ablative thermal alteration or damage (e.g., via sustained heating and/or resistive heating) to partially or completely disrupt the ability of a nerve to transmit a signal. Desired thermal heating effects, for example, may include raising the temperature of target neural fibers above a desired threshold to achieve non-ablative thermal alteration, or above a higher temperature to achieve ablative thermal alteration. For example, the target temperature can be above body temperature (e.g., approximately 37° C.) but less than about 45° C. for non-ablative thermal alteration, or the target temperature can be about 45° C. or higher for ablative thermal alteration. More specifically, exposure to thermal energy in excess of a body temperature of about 37° C., but below a temperature of about 45° C., may induce thermal alteration via moderate heating of target neural fibers or of vascular structures that perfuse the target fibers. In cases where vascular structures are affected, the target neural fibers may be denied perfusion resulting in necrosis of the neural tissue. For example, this may induce non-ablative thermal alteration in the fibers or structures. Exposure to heat above a temperature of about 45° C., or above about 60° C., may induce thermal alteration via substantial heating of the fibers or structures. For example, such higher temperatures may thermally ablate the target neural fibers or the vascular structures that perfuse the target fibers. In some patients, it may be desirable to achieve temperatures that thermally ablate the target neural fibers or the vascular structures, but that are less than about 90° C., or less than about 85° C., or less than about 80° C., and/or less than about 75° C. Other embodiments can include heating tissue to a variety of other suitable temperatures.

In some embodiments, ovarian neuromodulation can include a chemical-based treatment modality alone or in combination with another treatment modality. Neuromodulation using chemical-based treatment can include delivering one or more chemicals (e.g., drugs or other agents) to tissue at a treatment location in a manner that modulates neural function. The chemical, for example, can be selected to affect the treatment location generally or to selectively affect some structures at the treatment location over other structures. For example, the chemical can be guanethidine, ethanol, phenol, vincristine, neurotoxin, or another suitable agent selected to alter, damage, or disrupt nerves. In some embodiments, energy (e.g., light, ultrasound, or another suitable type of energy) can be used to activate the chemical and/or to cause the chemical to become more bioavailable. A variety of suitable techniques can be used to deliver chemicals to tissue at a treatment location. For example, chemicals can be delivered via one or more devices, such as needles originating outside the body or within the vasculature or delivery pumps (see, e.g., U.S. Pat. No. 6,978,174, the disclosure of which is hereby incorporated by reference in its entirety). In an intravascular example, a catheter can be used to intravascularly position a therapeutic element including a plurality of needles (e.g., micro-needles) that can be retracted or otherwise blocked prior to deployment. In other embodiments, a chemical can be introduced into tissue at a treatment location via simple diffusion through a vessel wall, electrophoresis, or another suitable mechanism. Similar techniques can be used to introduce chemicals that are not configured to cause neuromodulation, but rather to facilitate neuromodulation via another treatment modality. Examples of such chemicals include, but are not limited to, anesthetic agents and contrast agents.

In some embodiments, a treatment procedure can include applying a suitable treatment modality at a treatment location in a testing step followed by a treatment step. The testing step, for example, can include applying the treatment modality at a lower intensity and/or fix a shorter duration than during the treatment step. This can allow an operator to determine (e.g., by neural activity sensors and/or patient feedback) whether nerves proximate the treatment location are suitable for modulation. Performing a testing step can be particularly useful for treatment procedures in which targeted nerves are closely associated with nerves that could cause undesirable side effects if modulated during a subsequent treatment step.

B. Achieving Intravascular Access to the Ovarian Artery

Figures 2A, 2B:
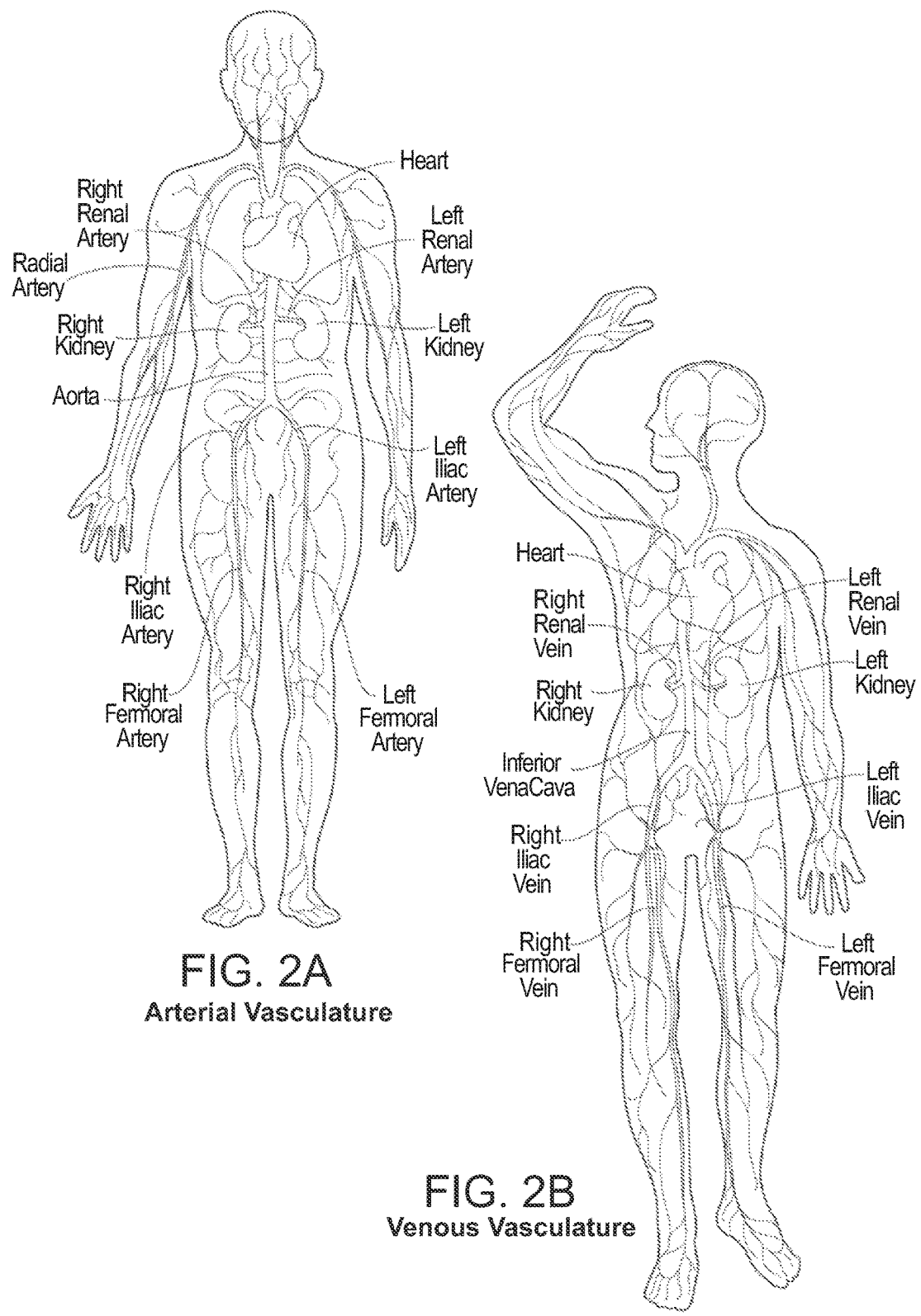
FIGS. 2A and 2B are anatomic views of the arterial vasculature and venous vasculature, respectively, of a human.

In accordance with the present technology, neuromodulation of a left and/or right ovarian nerve (e.g., ovarian plexus), which is intimately associated with a left and/or right ovarian artery 12 (FIG. 1A), may be achieved through intravascular access. As FIG. 2A shows, blood moved by contractions of the heart is conveyed from the left ventricle of the heart by the aorta. The aorta descends through the thorax and bifurcates at the left and right iliac arteries. The left and right iliac arteries descend, respectively, through the left and right legs and join the left and right femoral arteries.

As FIG. 2B shows, the blood collects in veins and returns to the heart, through the femoral veins into the iliac veins and into the inferior vena cava. Above the renal veins, the inferior vena cava ascends to convey blood into the right atrium of the heart. From the right atrium, the blood is pumped through the right ventricle into the lungs, where it is oxygenated. From the lungs, the oxygenated blood is conveyed into the left atrium. From the left atrium, the oxygenated blood is conveyed by the left ventricle back to the aorta.

As will be described in greater detail later, the femoral artery may be accessed and cannulated at the base of the femoral triangle just inferior to the midpoint of the inguinal ligament. A catheter (not shown) may be inserted percutaneously into the femoral artery through this access site, passed through the iliac artery and aorta, and placed into either the left or right ovarian artery 12 (FIG. 1A). This route comprises an intravascular path that offers minimally invasive access to a respective ovarian artery 12 and/or other ovarian blood vessels.

Another location for introduction of a catheter in the arterial system is through the femoral artery (as described above), passed through to the internal iliac artery, through the uterine artery, to the ovarian artery. Alternatively, the wrist, upper arm, and shoulder region provide other locations for introduction of catheters into the arterial system. For example, catheterization of either the radial, brachial, or axillary artery may be utilized in select cases. Catheters introduced via these access points may be passed through the subclavian artery on the left side (or via the subclavian and brachiocephalic arteries on the right side), through the aortic arch, down the descending aorta and into the ovarian arteries using standard angiographic technique.

C. Properties and Characteristics of the Ovarian Vasculature

Properties and characteristics of the ovarian and/or uterine vasculature impose challenges to both access and treatment methods, and to system/device designs. Since neuromodulation of a left and/or right ovarian nerve (e.g., ovarian plexus) may be achieved in accordance with embodiments of the present technology through intravascular access, various aspects of the design of apparatus, systems, and methods for achieving such ovarian neuromodulation are disclosed herein. Aspects of the technology disclosed herein address additional challenges associated with variation of physiological conditions and architecture across the patient population and/or within a specific patient across time, as well as in response to disease states, such as PCOS. For example, the design of the intravascular device and treatment protocols can address not only material/mechanical, spatial, fluid dynamic/hemodynamic and/or thermodynamic properties, but also pro vide particular algorithms and feedback protocols for delivering energy and obtaining real-time confirmatory results of successfully delivering energy to an intended target location in a patient-specific manner.

As discussed previously, a catheter may be advanced percutaneously into either the left or right ovarian artery via a minimally invasive intravascular path. However, minimally invasive ovarian arterial access may be challenging, for example, because as compared to some other arteries that are routinely accessed using catheters, the ovarian arteries can be tortuous, may be of relatively small diameter, and/or may require adjustments to the length and flexibility of the catheters. Ovarian arterial anatomy also may vary significantly from patient to patient, which further complicates minimally invasive access. Significant inter-patient variation may be seen, for example, in relative tortuosity, diameter, and/or length. Apparatus, systems and methods for achieving ovarian neuromodulation via intravascular access can account for these and other aspects of ovarian arterial anatomy and its variation across the patient population when minimally invasively accessing an ovarian artery. For example, spiral or helical computed tomography (CT) technology can be used to produce 3D images of the vascular features for individual patients, and intravascular path choice and as well as device size/diameter, length, flexibility, etc. can be selected based upon the patient's specific vascular features.

In addition to complicating ovarian arterial access, specifics of the ovarian anatomy also complicate establishment of stable contact between neuromodulatory apparatus and a luminal surface or wall of an ovarian artery. When the neuromodulatory apparatus includes an energy delivery element, such as an electrode, transducer, heating element or a cryotherapeutic device, consistent positioning and appropriate contact three applied by the energy or cryotherapy delivery element to the vessel wall, and adhesion between the applicator and the vessel wall can be important for predictability. However, navigation can be impeded by the tight space within an ovarian artery, as well as tortuosity of the artery. Furthermore, establishing consistent contact can be complicated by patient movement, respiration, and/or the cardiac cycle because these factors may cause significant movement of the ovarian artery relative to the aorta, and the cardiac cycle may transiently distend the ovarian artery (i.e., cause the wall of the artery to pulse). To address these challenges, the treatment device or applicator may be designed with relative sizing and flexibility considerations. For example, the ovarian artery may have an internal diameter less than approximately 1.7 mm and the treatment device can be delivered using a 3 French, or in some cases, a 4 French sized catheter. To address challenges associated with patient and/or arterial movement during treatment, the treatment device and neuromodulation system can be configured to use sensory feedback, such as impedance and temperature, to detect instability and to alert the operator to reposition the device and/or to temporarily stop treatment. In other embodiments, energy delivery algorithms can be varied in real-time to account for changes detected due to patient and/or arterial movement. In further examples, the treatment device may include one or more modifications or movement resistant enhancements such as atraumatic friction knobs or barbs on an outside surface of the device for resisting movement of the device relative to the desired tissue location, positionable balloons for inflating and holding the device in a consistent and stable position during treatment, or the device can include a cryogenic component that can temporarily freeze or adhere the device to the desired tissue location.

After accessing an ovarian artery 12 (FIGS. 1A and 1B) and facilitating stable contact between neuromodulatory apparatus and a luminal surface of the artery, nerves in and around the adventitia of the artery can be modulated via the neuromodulatory apparatus. Effectively applying thermal treatment from within an ovarian artery is non-trivial given the potential clinical complications associated with such treatment. For example, the intima and media of the ovarian artery are highly vulnerable to thermal injury. As discussed in greater detail below, the intima-media thickness separating the vessel lumen from its adventitia means that target ovarian nerves may be multiple millimeters distant (e.g., 1-3 mm) from the luminal surface of the artery. Sufficient energy can be delivered to or heat removed from the target ovarian nerves to modulate the target ovarian nerves without excessively cooling or heating the vessel wall to the extent that the wall is frozen, desiccated, or otherwise potentially affected to an undesirable extent. For example, when employing energy modalities such as RF or ultrasound, energy delivery can be focused on a location further from the interior vessel wall. In one embodiment, the majority of the RF or ultrasound energy can be focused on a location (e.g., a "hot spot") 1-3 mm beyond the interior surface of the vessel wall. The energy will dissipate from the hot spot in a radially decreasing manner. Thus, the targeted nerves can be modulated without damage to the luminal surface of the vessel. A potential clinical complication associated with excessive heating is thrombus formation from coagulating blood flowing through the artery. Given that this thrombus may cause irreversible damage to the ovary, thermal treatment from within the ovarian artery can be applied carefully. Accordingly, the complex fluid mechanics and thermodynamic conditions present in the ovarian artery during treatment, particularly those that may impact heat transfer dynamics at the treatment site, may be important in applying energy (e.g., heating thermal energy) and/or removing heat from the tissue (e.g., cooling thermal conditions) from within the ovarian artery.

The neuromodulatory apparatus can also be configured to allow for adjustable positioning and repositioning of an energy delivery element or a cryotherapeutic device within the ovarian artery since location of treatment may also impact clinical efficacy. For example, it may be tempting to apply a full circumferential treatment from within the ovarian artery given that the ovarian nerves may be spaced circumferentially around an ovarian artery. In some situations, a full-circle lesion likely resulting from a continuous circumferential treatment may be potentially related to ovarian artery stenosis. Therefore, the formation of more complex lesions along a longitudinal dimension of the ovarian artery via the cryotherapeutic devices or energy delivery elements and/or repositioning of the neuromodulatory apparatus to multiple treatment locations may be desirable. It should be noted, however, that a benefit of forming a circumferential lesion or ablation may outweigh the potential of ovarian artery stenosis or the risk may be mitigated with certain embodiments or in certain patients and forming a circumferential lesion or ablation could be a goal. Additionally, variable positioning and repositioning of the neuromodulatory apparatus may prove to be useful in circumstances where the ovarian artery is particularly tortuous or where there are proximal branch vessels off the ovarian artery main vessel, making treatment in certain locations challenging.

Blood flow through an ovarian artery may be temporarily occluded fix a short time with minimal or no complications. However, occlusion for a significant amount of time can be avoided in some cases to prevent injury to the ovary such as ischemia. It can be beneficial to avoid occlusion altogether or, if occlusion is beneficial, to limit the duration of occlusion (e.g., 2-5 minutes).

III. METHODS FOR TREATMENT OF POLYCYSTIC OVARY SYNDROME

Disclosed herein are several embodiments of methods directed to treatment of PCOS and related conditions using ovarian neuromodulation. The methods disclosed herein may represent various advantages over a number of conventional approaches and techniques in that they allow for the potential targeting of elevated sympathetic drive, which may either be a cause of PCOS or a key mediator of the multiple manifestations of the disease. Also, the disclosed methods provide for localized treatment and limited duration treatment regimens (e.g., one-time treatment), thereby reducing patient long-term treatment compliance issues.

In certain embodiments, the methods provided herein comprise performing ovarian neuromodulation thereby decreasing sympathetic ovarian nerve activity. Ovarian neuromodulation may be repeated one or more times at various intervals until a desired sympathetic nerve activity level or another therapeutic benchmark is reached. In one embodiment, for example, a decrease in sympathetic nerve activity may be observed via a marker of sympathetic nerve activity in PCOS patients, such as decreased levels of plasma norepinephrine (noradrenaline). Other measures or markers of sympathetic nerve activity can include MSNA, norepinephrine spillover, and/or heart rate variability. In another embodiment, other measurable physiological parameters or markers, such as a reduction in androgen production (e.g., lower testosterone levels) and associated symptoms (e.g., acne, hirsutism), increased regularity of menstruation, ovulation, decrease in number of ovarian cysts, reduction in pain level perceived by the PCOS patient, improved blood pressure control, improved blood glucose regulation, etc., can be used to assess efficacy of the thermal undulation treatment for PCOS patients.

In certain embodiments of the methods provided herein, ovarian neuromodulation is expected to result in a change in sympathetic nerve activity over a specific timeframe. For example, in certain of these embodiments, sympathetic nerve activity levels are decreased over an extended timeframe, e.g., within 1 month, 2 months, 3 months, 6 months, 9 months or 12 months post-neuromodulation.

In several embodiments, the methods disclosed herein may comprise an additional step of measuring sympathetic nerve activity levels, and in certain of these embodiments, the methods can further comprise comparing the activity level to a baseline activity level. Such comparisons can be used to monitor therapeutic efficacy and to determine when and if to repeat the neuromodulation procedure. In certain embodiments, a baseline sympathetic nerve activity level is derived from the subject undergoing treatment. For example, baseline sympathetic nerve activity level may be measured in the subject at one or more timepoints prior to treatment. A baseline sympathetic nerve activity value may represent sympathetic nerve activity at a specific timepoint before neuromodulation, or it may represent an average activity level at two or more timepoints prior to neuromodulation. In certain embodiments, the baseline value is based on sympathetic nerve activity immediately prior to treatment (e.g., after the subject has already been catheterized). Alternatively, a baseline value may be derived from a standard value for sympathetic nerve activity observed across the population as a whole or across a particular subpopulation. In certain embodiments, post-neuromodulation sympathetic nerve activity levels are measured in extended timeframes post-neuromodulation, e.g., 3 months, 6 months or 12 months post-neuromodulation.

In certain embodiments of the methods provided herein, the methods are designed to decrease sympathetic nerve activity to a target level. In these embodiments, the methods include a step of measuring sympathetic nerve activity levels post-neuromodulation (e.g., 6 months post-treatment, 12 months post-treatment, etc.) and comparing the resultant activity level to a baseline activity level as discussed above. In certain of these embodiments, the treatment is repeated until the target sympathetic nerve activity level is reached. In other embodiments, the methods are simply designed to decrease sympathetic nerve activity below a baseline level without requiring a particular target activity level.

Ovarian neuromodulation may be performed on a patient diagnosed with PCOS to reduce one or more measurable physiological parameters corresponding to the PCOS. In some embodiments, for example, ovarian neuromodulation may prevent, increase, maintain, or reduce the number of ovarian cysts (e.g., immature ovarian follicles). A reduction in the number of ovarian cysts can be, for example, at least about 5%, 10%, or a greater amount as determined by qualitative or quantitative analysis (e.g., ultrasound) before and after (e.g., 1, 3, 6, or 12 months after) an ovarian neuromodulation procedure. In other embodiments, ovarian neuromodulation may prevent expansion of maintain, or reduce an ovarian cyst size with regard to a particular ovarian cyst or an average size of some or all ovarian cysts in a patient. A reduction in ovarian cyst size can be, for example, at least about 5%, 10%, or a greater amount as determined by qualitative or quantitative analysis (e.g., ultrasound) before and after (e.g., 1, 3, 6, or 12 months after) an ovarian neuromodulation procedure. In other embodiments, abnormally large ovarian size (>10 $cm^3$) may be normalized (or brought closer to a normal range).

In addition to or instead of affecting the growth or size of one or more cysts in a patient, ovarian neuromodulation may efficaciously treat other measurable physiological parameter(s) or sequela(e) corresponding to PCOS. For example, in some embodiments, ovarian neuromodulation may reduce the severity and/or frequency of pain, reproductive/fertility issues (e.g., oligo/amenorrhea, infertility, acne and hirsutism), metabolic issues (e.g., obesity, metabolic syndrome, insulin resistance), and cardiovascular risk (e.g., high cholesterol, hypertension). These and other results can occur at various times, e.g., directly following ovarian neuromodulation or within about 1 month, 3 months, 6 months, a year, or a longer period following ovarian neuromodulation.

As discussed previously, the progression of PCOS may be related to sympathetic overactivity and, correspondingly, the degree of sympathoexcitation in a patient may be related to the severity of the clinical presentation of the PCOS. The ovaries may be positioned to be both a cause (via afferent nerve fibers) and a target (via efferent sympathetic nerves) of elevated central sympathetic drive. In some embodiments, ovarian neuromodulation can be used to reduce central sympathetic drive in a patient diagnosed with PCOS in a manner that treats the patient for the PCOS. In some embodiments, for example, MSNA can be reduced by at least about 10% in the patient within about three months after at least partially inhibiting sympathetic neural activity in nerves proximate an ovarian artery innervating the ovary. Similarly, in some instances ovarian norepinephrine spillover to plasma can be reduced at least about 20% in the patient within about three months after at least partially inhibiting sympathetic neural activity in nerves proximate an ovarian artery innervating the ovary. Additionally, measured ovarian norepinephrine content (e.g., assessed via biopsy, assessed in real-time via intravascular blood collection techniques, etc.) can be reduced (e.g., at least about 5%, 10%, or by at least 20%) in the patient within about three months after at least partially inhibiting sympathetic neural activity in nerves proximate an ovarian artery innervating the ovary.

In one prophetic example, a patient diagnosed with PCOS can be subjected to a baseline assessment indicating a first set of measurable parameters corresponding to the PCOS. Such parameters can include, for example, blood pressure, cholesterol levels, blood glucose levels, fasting blood insulin levels, measures of insulin sensitivity, duration/frequency of menses, testosterone levels, FSH/LH (luteinizing hormone) levels, perceived pain level, aldosterone levels, severity of hirsutism, and severity of acne. The patient also can be tested (e.g., using ultrasound) to determine a baseline size and number of cysts of the ovaries and baseline ovary size and/or volume. Following baseline assessment, the patient can be subjected to an ovarian neuromodulation procedure. Such a procedure can, for example, include any of the treatment modalities described herein or another treatment modality in accordance with the present technology. The treatment can be performed on nerves proximate one or both ovaries of the patient. Following the treatment (e.g., 1, 3, 6, or 12 months following the treatment), the patient can be subjected to a follow-up assessment. The follow-up assessment can indicate a measurable improvement in one or more physiological parameters corresponding to the PCOS.

The methods described herein address the sympathetic excess that is thought to be an underlying cause of PCOS or a central mechanism through which PCOS manifests its multiple deleterious effects on patients. In contrast, known therapies currently prescribed for PCOS patients typically address only specific manifestations of PCOS. Additionally, these known therapies can have significant limitations including limited efficacy, undesirable side effects and can be subject to adverse or undesirable drug interactions when used in combination. Additionally, conventional therapies require the patient to remain compliant with the treatment regimen over time. In contrast, ovarian neuromodulation can be a one-time treatment that would be expected to have durable benefits to inhibit the long-term disease progression and thereby achieve a favorable patient outcome.

In some embodiments, patients diagnosed with PCOS can be treated with ovarian neuromodulation alone. However, in other embodiments, patients diagnosed with PCOS can be treated with combinations of therapies for treating both primary causative modes of PCOS as well as sequelae of PCOS. For example, combinations of therapies can be tailored based on specific manifestations of the disease in a particular patient. In a specific example, patients having PCOS and presenting hypertension can be treated with both anti-hypertensive therapy (e.g., drugs) and ovarian neuromodulation. In another example, ovarian neuromodulation can be combined with cholesterol lowering agents (e.g., statins), hormonal therapy (e.g., estrogen-progestin contraceptive), fertility treatments (e.g., clomiphene, dexamethasone, FSH injections, ovarian surgery, in vitro fertilization), antiandrogens (e.g., spironolactone, finasteride, cyproterone acetate, GnRH agonists), acne-focused antibiotics, anti-acne treatments, hair growth inhibitors (e.g., eflornithine hydrochloride) and depilatories for hirsutism as well as weight loss and lifestyle change recommendations/programs.

Treatment of PCOS or related conditions may refer to preventing the condition, slowing the onset or rate of development of the condition, reducing the risk of developing the condition, preventing or delaying the development of symptoms associated with the condition, reducing or ending symptoms associated with the condition generating a complete or partial regression of the condition, or some combination thereof.

IV. SELECTED EMBODIMENTS OF OVARIAN NEUROMODULATION SYSTEMS AND DEVICES

Figure 3:
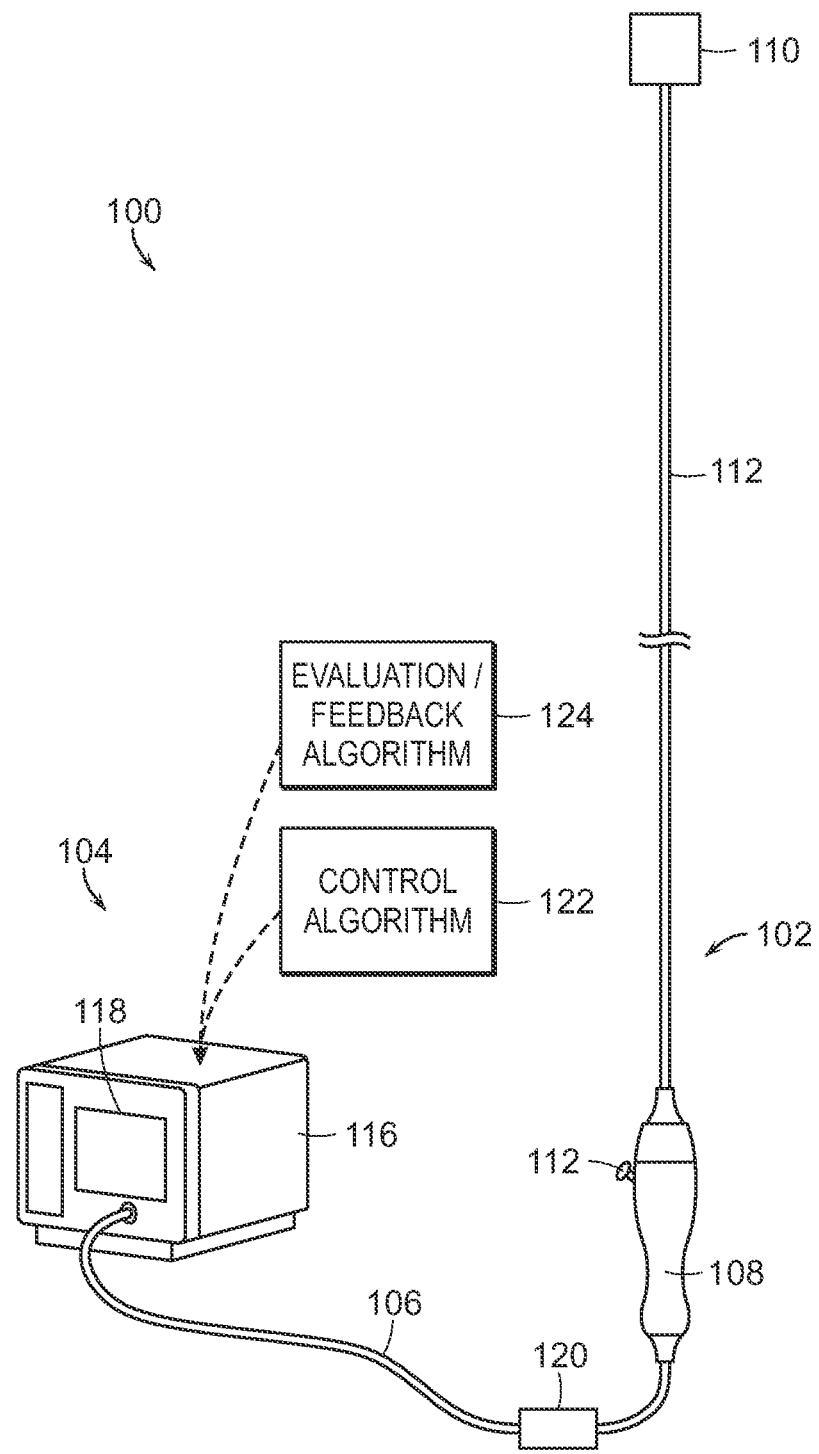
FIG. 3 illustrates an intravascular neuromodulation system configured in accordance with an embodiment of the present technology.

FIG. 3 is a partially schematic diagram illustrating a neuromodulation system 100 ("system 100") configured in accordance with an embodiment of the present technology. The system 100 can include a treatment device 102, an energy source or console 104 (e.g., a RF energy generator, a cryotherapy console, etc.), and a cable 106 extending between the treatment device 102 and the console 104. The treatment device 102 can include a handle 108, a neuromodulation assembly 110, and an elongated shaft 112 extending between the handle 108 and the neuromodulation assembly 110. The shaft 112 can be configured to locate the neuromodulation assembly 110 intravascularly at a treatment location (e.g., in or near the ovarian artery, the ovarian vein, and/or another suitable structure), and the neuromodulation assembly 110 can be configured to provide or support therapeutically-effective neuromodulation at the treatment location. In some embodiments, the shaft 112 and the neuromodulation assembly 110 can be 3, 4, 5, 6, or 7 French or another suitable size. Furthermore, the shaft 112 and the neuromodulation assembly 110 can be partially or fully radiopaque and/or can include radiopaque markers corresponding to measurements, e.g., every 5 cm.

Intravascular delivery can include percutaneously inserting a guide wire (not shown) within the vasculature and moving the shaft 112 and the neuromodulation assembly 110 along the guide wire until the neuromodulation assembly 110 reaches the treatment location. For example, the shaft 112 and the neuromodulation assembly 110 can include a guide-wire lumen (not shown) configured to receive the guide wire in an over-the-wire (OTW) or rapid-exchange (RX) configuration. Other body lumens (e.g., ducts or internal chambers) can be treated, for example, by non-percutaneously passing the shaft 112 and neuromodulation assembly 110 through externally accessible passages of the body or other suitable methods. In some embodiments, a distal end of the neuromodulation assembly 110 can terminate in an atraumatic rounded tip or cap (not shown). The treatment device 102 can also be a steerable or non-steerable catheter device (e.g., a guide catheter) configured for use without a guide wire.

The neuromodulation assembly 110 can have a single state or configuration, or it can be convertible between a plurality of states or configurations. For example, the neuromodulation assembly 110 can be configured to be delivered to the treatment location in a delivery state and to provide or support therapeutically-effective neuromodulation in a deployed state. In these and other embodiments, the neuromodulation assembly 110 can have different sizes and/or shapes in the delivery and deployed states. For example, the neuromodulation assembly 110 can have a low-profile configuration in the delivery state and an expanded configuration in the deployed state. In another example, the neuromodulation assembly 110 can be configured to deflect into contact with a vessel wall in a delivery state. The neuromodulation assembly 110 can be converted (e.g., placed or transformed) between the delivery and deployed states via remote actuation, e.g., using an actuator 114 of the handle 108. The actuator 114 can include a knob, a pin, a lever, a button, a dial, or another suitable control component. In other embodiments, the neuromodulation assembly 110 can be transformed between the delivery and deployed states using other suitable mechanisms or techniques.

In some embodiments, the neuromodulation assembly 110 can include an elongated member (not shown) that can be configured to curve (e.g., arch) in the deployed state, e.g., in response to movement of the actuator 114. For example, the elongated member can be at least partially helical/spiral in the deployed state. In other embodiments, the neuromodulation assembly 110 can include a balloon (not shown) that can be configured to be at least partially inflated in the deployed state. An elongated member, for example, can be well suited for carrying one or more heating elements, electrodes or transducers and for delivering direct heat, electrode-based or transducer-based treatment. A balloon, for example, can be well suited for containing refrigerant (e.g., during or shortly after liquid-to-gas phase change) and for delivering cryotherapeutic treatment. A balloon can also be used in some embodiments for carrying suitable RF conducting electrodes. In some embodiments, the neuromodulation assembly 110 can be configured for intravascular and/or transvascular delivery of chemicals. For example, the neuromodulation assembly 110 can include one or more openings (not shown), and chemicals (e.g., drugs or other agents) can be deliverable through the openings. For transvascular delivery, the neuromodulation assembly 110 can include one or more needles (not shown) (e.g., retractable needles) and the openings can be at end portions of the needles.

The console 104 is configured to control, monitor, supply, or otherwise support operation of the treatment device 102.

In some embodiments, the console 104 can be separate from and in communication with the treatment device 102. In other embodiments, the console 104 can be contained within or be a component of the treatment device 102. In still further embodiments, the treatment device 102 can be self-contained and/or otherwise configured for operation without connection to the console 104. As shown in FIG. 3, the console 104 can include a primary housing 116 having a display 118. The system 100 can include a control device 120 along the cable 106 configured to initiate, terminate, and/or adjust operation of the treatment device 102 directly and/or via the console 104. In other embodiments, the system 100 can include another suitable control mechanism. For example, the control device 120 can be incorporated into the handle 108. The console 104 can be configured to execute an automated control algorithm 122 and/or to receive control instructions from an operator. Furthermore, the console 104 can be configured to provide feedback to an operator before, during, and/or after a treatment procedure via the display 118 and/or an evaluation/feedback algorithm 124. In some embodiments, the console 104 can include a processing device (not shown) having processing circuitry, e.g., a microprocessor. The processing device can be configured to execute stored instructions relating to the control algorithm 122 and/or the evaluation/feedback algorithm 124. Furthermore, the console 104 can be configured to communicate with the treatment device 102, e.g., via the cable 106. For example, the neuromodulation assembly 110 of the treatment device 102 can include a sensor (not shown) (e.g., a recording electrode, a temperature sensor, a pressure sensor, or a flow rate sensor) and a sensor lead (not shown) (e.g., an electrical lead or a pressure lead) configured to carry a signal from the sensor to the handle 108. The cable 106 can be configured to carry the signal from the handle 108 to the console 104.

The console 104 can have different configurations depending on the treatment modality of the treatment device 102. For example, when the treatment device 102 is configured for electrode-based or transducer-based treatment, the console 104 can include an energy generator (not shown) configured to generate RF energy, pulsed RF energy, microwave energy, optical energy, ultrasound energy (e.g., intravascularly delivered ultrasound, extracorporeal ultrasound, HIFU), magnetic energy, direct heat energy, or another suitable type of energy. In some embodiments, for example, the console 104 can include a RF generator operably coupled to one or more electrodes (not shown) of the neuromodulation assembly 110.

When the treatment device 102 is configured for cryotherapeutic treatment, the console 104 can include a refrigerant reservoir (not shown) and can be configured to supply the treatment device 102 with refrigerant, e.g., pressurized refrigerant in liquid or substantially liquid phase. Similarly, when the treatment device 102 is configured for chemical-based treatment, the console 104 can include a chemical reservoir (not shown) and can be configured to supply the treatment device 102 with one or more chemicals. In some embodiments, the treatment device 102 can include an adapter (not shown) (e.g., a luer lock) configured to be operably coupled to a syringe (not shown). The adapter can be fluidly connected to a lumen (not shown) of the treatment device 102, and the syringe can be used, for example, to manually deliver one or more chemicals to the treatment location, to withdraw material from the treatment location, to inflate a balloon (not shown) of the neuromodulation assembly 110, to deflate a balloon of the neuromodulation assembly 110, or for another suitable purpose. In other embodiments, the console 104 can have other suitable configurations.

In certain embodiments, a neuromodulation device for use in the methods disclosed herein may combine two or more energy modalities. For example, the device may include both a hyperthermic source of ablative energy and a hypothermic source, making it capable of for example, performing both RF neuromodulation and cryo-neuromodulation. The distal end of the treatment device may be straight (for example, a focal catheter), expandable (for example, an expanding mesh or cryoballoon), or have any other configuration. For example, the distal end of the treatment device can be at least partially helical/spiral in the deployed state. Additionally or alternatively, the treatment device may be configured to carry out one or more non-ablative neuromodulatory techniques. For example, the device may comprise a means for diffusing a drug or pharmaceutical compound at the target treatment area (e.g., a distal spray nozzle).

V. SELECTED EXAMPLES OF TREATMENT PROCEDURES FOR OVARIAN NEUROMODULATION

Referring back to FIGS. 1A and 1B and in some embodiments, the shaft 18 and the therapeutic element 20 can be portions of a treatment device at least partially corresponding to the treatment device 102 shown in FIG. 3. The therapeutic element 20, for example, can be configured to radially expand into a deployed state at the treatment location. In the deployed state, the therapeutic element 20 can be configured to contact an inner wall of a vessel of the ovarian vasculature and to form a suitable lesion or pattern of lesions without the need for repositioning. For example, the therapeutic element 20 can be configured to form a single lesion or a series of lesions, e.g., overlapping or non-overlapping. In some embodiments, the lesion or pattern of lesions can extend around generally the entire circumference of the vessel, but can still be non-circumferential at longitudinal segments or zones along a lengthwise portion of the vessel. This can facilitate precise and efficient treatment with a low possibility of vessel stenosis. In other embodiments, the therapeutic element 20 can be configured form a partially-circumferential lesion or a fully-circumferential lesion at a single longitudinal segment or zone of the vessel. During treatment, the therapeutic element 20 can be configured for partial or full occlusion of a vessel. Partial occlusion can be useful, for example, to reduce ovarian ischemia, while full occlusion can be useful, for example, to reduce interference (e.g., warming or cooling) caused by blood flow through the treatment location. In some embodiments, the therapeutic element 20 can be configured to cause therapeutically-effective neuromodulation (e.g., using ultrasound energy) without contacting a vessel wall.

A variety of other suitable treatment locations are also possible in and around the ovarian artery 12, the ovarian vein 14, and/or other suitable structures. For example, since the ovarian artery 12 becomes narrower and more tortuous further from the aorta, it can be more convenient in some cases to treat the ovarian artery 12 at its trunk. Furthermore, a treatment procedure can include treatment at any suitable number of treatment locations, e.g., a single treatment location, two treatment locations, or more than two treatment locations. In some embodiments, different treatment locations can correspond to different portions of the ovarian artery 12, the ovarian vein, and/or other suitable structures proximate tissue having relatively high concentrations of ovarian nerves. The shaft 18 can be steerable (e.g., via one or more pull wires, a steerable guide or sheath catheter, etc.) and can be configured to move the therapeutic element 20 between treatment locations. At each treatment location, the therapeutic element 20 can be activated to cause modulation of nerves proximate the treatment location. Activating the therapeutic element 20 can include, for example, heating, cooling, stimulating, or applying another suitable treatment modality at the treatment location. Activating the therapeutic element 20 can further include applying various energy modalities at varying power levels, intensities and for various durations for achieving modulation of nerves proximate the treatment location. In some embodiments, power levels, intensities and/or treatment duration can be determined and employed using various algorithms for ensuring modulation of nerves at select distances (e.g., depths) away from the treatment location. Furthermore, as noted previously, in some embodiments, the therapeutic element 20 can be configured to introduce (e.g., inject) a chemical (e.g., a drug or other agent) into target tissue at the treatment location. Such chemicals or agents can be applied at various concentrations depending on treatment location and the relative depth of the target nerves.

The therapeutic element 20 can be positioned at a treatment location within the ovarian artery 12, for example, via a catheterization path including a femoral artery and the aorta, a catheterization path including the internal iliac artery and the uterine artery, or another suitable catheterization path, e.g., a radiator brachial catheterization path. Catheterization can be guided, for example, using imaging, e.g., magnetic resonance, computed tomography, fluoroscopy, ultrasound, intravascular ultrasound, optical coherence tomography, or another suitable imaging modality. The therapeutic element 20 can be configured to accommodate the anatomy of the ovarian artery 12, the ovarian vein 14, and/or another suitable structure. For example, the therapeutic element 20 can include a balloon (not shown) configured to inflate to a size generally corresponding to the internal size of the ovarian artery 12, the ovarian vein 14, and/or another suitable structure. In some embodiments, the therapeutic element 20 can be an implantable device and a treatment procedure can include locating the therapeutic element 20 at the treatment location using the shaft 18 fixing the therapeutic element 20 at the treatment location, separating the therapeutic element 20 from the shaft 18, and withdrawing the shaft 18. Other treatment procedures for modulation of ovarian nerves in accordance with embodiments of the present technology are also possible.

As mentioned previously, the methods disclosed herein may use a variety of suitable energy modalities, including RF energy, microwave energy, laser, optical energy, ultrasound energy (e.g., intravascularly delivered ultrasound, extracorporeal ultrasound, HIFU), magnetic energy, direct heat, cryotherapy, or a combination thereof. Alternatively or in addition to these techniques, the methods may utilize one or more non-ablative neuromodulatory techniques. For example, the methods may utilize non-ablative SNS neuromodulation by removal of target nerves (e.g., surgically), injection of target nerves with a destructive drug or pharmaceutical compound, or treatment of the target nerves with non-ablative energy modalities (e.g., laser or light energy). In certain embodiments, the amount of reduction of the sympathetic nerve activity may vary depending on the specific technique being used.

Figure 4:
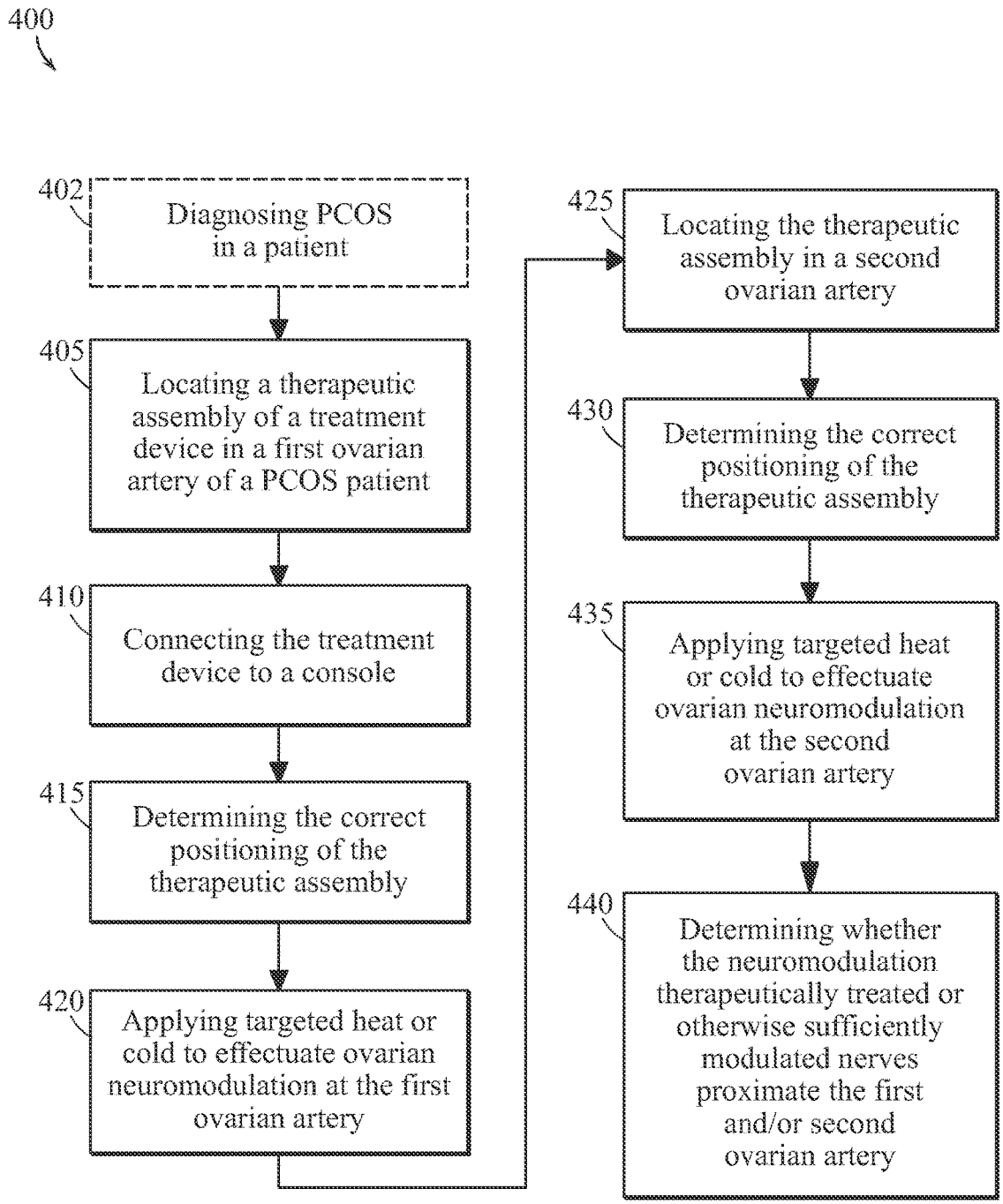
FIG. 4 is a block diagram illustrating a method of modulating ovarian nerves in accordance with an embodiment of the present technology.

FIG. 4 is a block diagram illustrating a method 400 of modulating ovarian nerves using the system 100 described above with reference to FIGS. 1A-3. With reference to FIGS. 1A-4 together, the method 400 can optionally include diagnosing PCOS in a patient (if not yet determined) and/or selecting a suitable candidate PCOS patient for performing ovarian neuromodulation (block 402). The method 400 can include intravascularly locating the neuromodulation assembly 110 in a delivery state (e.g., low-profile configuration) at a first target site in or near a first ovarian blood vessel (e.g., first ovarian artery) (block 405). The treatment device 102 and/or portions thereof (e.g., the neuromodulation assembly 110) can be inserted into a guide catheter or sheath to facilitate intravascular delivery of the neuromodulation assembly 110. In certain embodiments, for example, the treatment device 102 can be configured to fit within an 8 Fr guide catheter or smaller (e.g., 7 Fr, 6 Fr, etc.) to access small peripheral vessels. A guide wire (not shown), if present, can be used to manipulate and enhance control of the shaft 112 and the neuromodulation assembly 110 (e.g., in an over-the-wire or a rapid-exchange configuration). In some embodiments, radiopaque markers and/or markings on the treatment device 102 and/or the guide wire can facilitate placement of the neuromodulation assembly 110 at the first target site (e.g., a first ovarian artery of a PCOS patient). In some embodiments, a contrast material can be delivered distally beyond the neuromodulation assembly 110, and fluoroscopy and/or other suitable imaging techniques can be used to aid in placement of the neuromodulation assembly 110 at the first target site.

The method 400 can further include connecting the treatment device 102 to the console 104 (block 410), and determining whether the neuromodulation assembly 110 is in the correct position at the target site and/or whether the neuromodulation assembly (e.g., electrodes or cryotherapy balloon) is functioning properly (block 415). Once the neuromodulation assembly 110 is properly located at the first target site and no malfunctions are detected, the console 104 can be manipulated to initiate application of an energy field to the target site to cause electrically-induced and/or thermally-induced partial or full denervation of the ovary (e.g., using electrodes or cryotherapeutic devices). Accordingly, heating and/or cooling of the neuromodulation assembly 110 causes modulation of ovarian nerves at the first target site to cause partial or full denervation of the ovary associated with the first target site (block 420).

In one example, the treatment device 102 can be an RF energy emitting device and RF energy can be delivered through energy delivery elements or electrodes to one or more locations along the inner wall of the first ovarian artery for predetermined periods of time (e.g., 120 seconds). In some embodiments, multiple treatments (e.g., 4-6) may be administered in both the left and right ovarian arteries to achieve a desired coverage. An objective of a treatment may be, for example, to heat tissue to a desired depth (e.g., at least about 3 mm) to a temperature (e.g., about 65° C.) that would modulate one or more nerve fibers associated with or adjacent to one or more lesions formed in the vessel wall. A clinical objective of the procedure typically is to neuromodulate a sufficient number of ovarian nerves (either efferent or afferent nerves) to cause a reduction in sympathetic tone or drive to the ovaries without, for example, disrupting ovarian function and while minimizing vessel trauma. If the objective of a treatment is met (e.g., tissue is heated to about 65° C. to a depth of about 3 mm) the probability of modulating ovarian nerve tissue (e.g., altering nerve function) is high. In some embodiments, a single neuromodulation treatment procedure can provide for sufficient modulation of target sympathetic nerves (e.g., modulation of a sufficient number of nerve fibers) to provide a desired clinical outcome. In other embodiments, more than one treatment may be beneficial for modulating a desired number or volume of target sympathetic nerve fibers, and thereby achieve clinical success. In other embodiments, an objective may include reducing or eliminating ovarian nerve function completely.

In a specific example of using RF energy for ovarian nerve modulation, a clinician can commence treatment which causes the control algorithm 122 (FIG. 3) to initiate instructions to the generator (not shown) to gradually adjust its power output to a first power level (e.g., 5 watts) over a first time period (e.g., 15 seconds). The power increase during the first time period is generally linear. As a result, the generator increases its power output at a generally constant rate of power/time, i.e., in a linear manner. Alternatively, the power increase may be non-linear (e.g., exponential or parabolic) with a variable rate of increase. Once the first power level and the first time are achieved, the algorithm may hold at the first power level until a second predetermined period of time has elapsed (e.g., 3 seconds). At the conclusion of the second period of time, power is again increased by a predetermined increment (e.g., 1 watt) to a second power level over a third predetermined period of time. (e.g., 1 second). This power ramp in predetermined increments of about 1 watt over predetermined periods of time may continue until a maximum power $P_{MAX}$ is achieved or some other condition is satisfied. In one embodiment, $P_{MAX}$ is 8 watts. In another embodiment, $P_{MAX}$ is 10 watts, or in a further embodiment, $P_{MAX}$ is 6.5 watts. In some embodiments, $P_{MAX}$ can be about 6 watts to about 10 watts. Optionally, the power may be maintained at the maximum power $P_{MAX}$ for a desired period of time or up to the desired total treatment time (e.g., up to about 120 seconds) or until a specified temperature is reached or maintained for a specified time period.

In another specific example, the treatment device 102 can be a cryogenic device and cryogenic cooling can be applied for one or more cycles (e.g., for 30 second increments, 60 second increments, 90 second increments, etc.) in one or more locations along the circumference and/or length of the first ovarian artery. The cooling cycles can be, for example, fixed periods or can be fully or partially dependent on detected temperatures (e.g., temperatures detected by a thermocouple (not shown) of the neuromodulation assembly 110). In some embodiments, a first stage can include cooling tissue until a first target temperature is reached. A second stage can include maintaining cooling in a set period, such as 15-180 seconds (e.g., 90 seconds). A third stage can include terminating or decreasing cooling to allow the tissue to warm to a second target temperature higher than the first target temperature. A fourth stage can include continuing to allow the tissue to warm for a set period, such as 10-120 seconds (e.g., 60 seconds). A fifth stage can include cooling the tissue until the first target temperature (or a different target temperature) is reached. A sixth stage can include maintaining cooling for a set period, such as 15-180 seconds (e.g., 90 seconds). A seventh stage can, for example, include allowing the tissue to warm completely (e.g., to reach a body temperature).

The neuromodulation assembly 110 can then be located at a second target site in or near a second ovarian blood vessel (e.g., second ovarian artery) (block 425), and correct positioning of the assembly 110 can be determined (block 430). In selected embodiments, a contrast material can be delivered distally beyond the neuromodulation assembly 110 and fluoroscopy and/or other suitable imaging techniques can be used to locate the second ovarian artery. The method 400 continues by applying targeted heat or cold to effectuate ovarian neuromodulation at the second target site to cause partial or full denervation of the ovary associated with the second target site (block 435).

After providing the therapeutically-effective neuromodulation energy (e.g., cryogenic cooling, RF energy, ultrasound energy, etc.), the method 400 may also include determining whether the neuromodulation therapeutically treated the patient for PCOS or otherwise sufficiently modulated nerves or other neural structures proximate the first and second target sites (block 440). For example, the process of determining whether the neuromodulation therapeutically treated the nerves can include determining whether nerves were sufficiently modulated or otherwise disrupted to reduce, suppress, inhibit, block or otherwise affect the afferent and/or efferent ovarian signals (e.g., by evaluation of suitable biomarkers, stimulation and recording of nerve signals, etc.), in a further embodiment, patient assessment could be performed at time intervals (e.g., 1 month, 3 months, 6 months, 12 months) following neuromodulation treatment. For example, the patient can be assessed for measurements of perceived pain, blood pressure control, blood glucose levels, androgen levels (e.g., testosterone levels), imaging-based measurements of ovarian cyst size and number, imaging-based measurements of ovary size and/or volume, reversal of infertility, regularity of menses, improvement in hirsutism, aldosterone levels, and measures of sympathetic activity (e.g., MSNA, and/or ovarian norepinephrine spillover to plasma, whole body norepinephrine spillover, and heart rate variability).

In other embodiments, various steps in the method 400 can be modified, omitted, and/or additional steps may be added. In further embodiments, the method 400 can have a delay between applying therapeutically-effective neuromodulation energy at a first target site at or near a first ovarian artery and applying therapeutically-effective neuromodulation energy at a second target site at or near a second ovarian artery. For example, neuromodulation of the first ovarian artery can take place at a first treatment session, and neuromodulation of the second ovarian artery can take place a second treatment session at a later time.

As discussed previously, treatment procedures for modulation of ovarian nerves in accordance with embodiments of the present technology are expected to improve at least one condition associated with ovarian sympathetic activity (e.g., overactivity or hyperactivity) and/or central sympathetic activity (e.g., overactivity or hyperactivity). For example, with respect to PCOS, modulation of ovarian nerves in accordance with embodiments of the present technology is expected to reduce expansion of maintain the size of or reduce the size of an ovarian cyst in a patient. In a particular example, the size of an ovarian cyst in a patient is expected to be reduced at least about 5% within about three months after modulating the ovarian nerves in the patient. With respect to central sympathetic activity (e.g., overactivity or hyperactivity), fir example, modulation of ovarian nerves is expected to reduce MSNA and/or whole body norepinephrine spillover in patients. These and other clinical effects are expected to be detectable immediately after a treatment procedure or after a delay, e.g., of 1, 2, or 3 months. In some instances, it may be useful to repeat ovarian neuromodulation at the same treatment location or a different treatment location after a suitable delay, e.g., 1, 2, or 3 years. In still other embodiments, however, other suitable treatment regimens or techniques may be used.

VI. PERTINENT ANATOMY AND PHYSIOLOGY

The following discussion provides further details regarding pertinent patient anatomy and physiology. This section is intended to supplement and expand upon the previous discussion regarding the relevant anatomy and physiology, and to provide additional context regarding the disclosed technology and the therapeutic benefits associated with ovarian neuromodulation.

A. The Sympathetic Nervous System

The SNS is a branch of the autonomic nervous system along with the enteric nervous system and parasympathetic nervous system. It is always active at a basal level (called sympathetic tone) and becomes more active during times of stress. Like other parts of the nervous system, the SNS operates through a series of interconnected neurons. Sympathetic neurons are frequently considered part of the peripheral nervous system (PNS), although many lie within the central nervous system (CNS). Sympathetic neurons of the spinal cord (which is part of the CNS) communicate with peripheral sympathetic neurons via a series of sympathetic ganglia. Within the ganglia, spinal cord sympathetic neurons join peripheral sympathetic neurons through synapses. Spinal cord sympathetic neurons are therefore called presynaptic (or preganglionic) neurons, while peripheral sympathetic neurons are called postsynaptic (or postganglionic) neurons.

At synapses within the sympathetic ganglia, preganglionic sympathetic neurons release acetylcholine, a chemical messenger that binds and activates nicotinic acetylcholine receptors on postganglionic neurons. In response to this stimulus, postganglionic neurons principally release noradrenaline (norepinephrine). Prolonged activation may elicit the release of adrenaline from the adrenal medulla.

Once released, norepinephrine binds adrenergic receptors on peripheral tissues. Binding to adrenergic receptors causes a neuronal and hormonal response. The physiologic manifestations include pupil dilation, increased heart rate, occasional vomiting, and increased blood pressure. Increased sweating is also seen due to binding of cholinergic receptors of the sweat glands.

The SNS is responsible for up- and down-regulation of many homeostatic mechanisms in living organisms. Fibers from the SNS innervate tissues in almost every organ system, providing at least some regulatory function to physiological features as diverse as pupil diameter, gut motility, and urinary output. This response is also known as the sympatho-adrenal response of the body, as the preganglionic sympathetic fibers that end in the adrenal medulla (but also all other sympathetic fibers) secrete acetylcholine, which activates the secretion of adrenaline (epinephrine) and to a lesser extent noradrenaline (norepinephrine). Therefore, this response that acts primarily on the cardiovascular system is mediated directly via impulses transmitted through the SNS and indirectly via catecholamines secreted from the adrenal medulla.

Science typically looks at the SNS as an automatic regulation system, that is, one that operates without the intervention of conscious thought. Some evolutionary theorists suggest that the SNS operated in early organisms to maintain survival as the SNS is responsible for priming the body for action. One example of this priming is in the moments before waking, in which sympathetic outflow spontaneously increases in preparation for action.

1. The Sympathetic Chain

Figure 5:
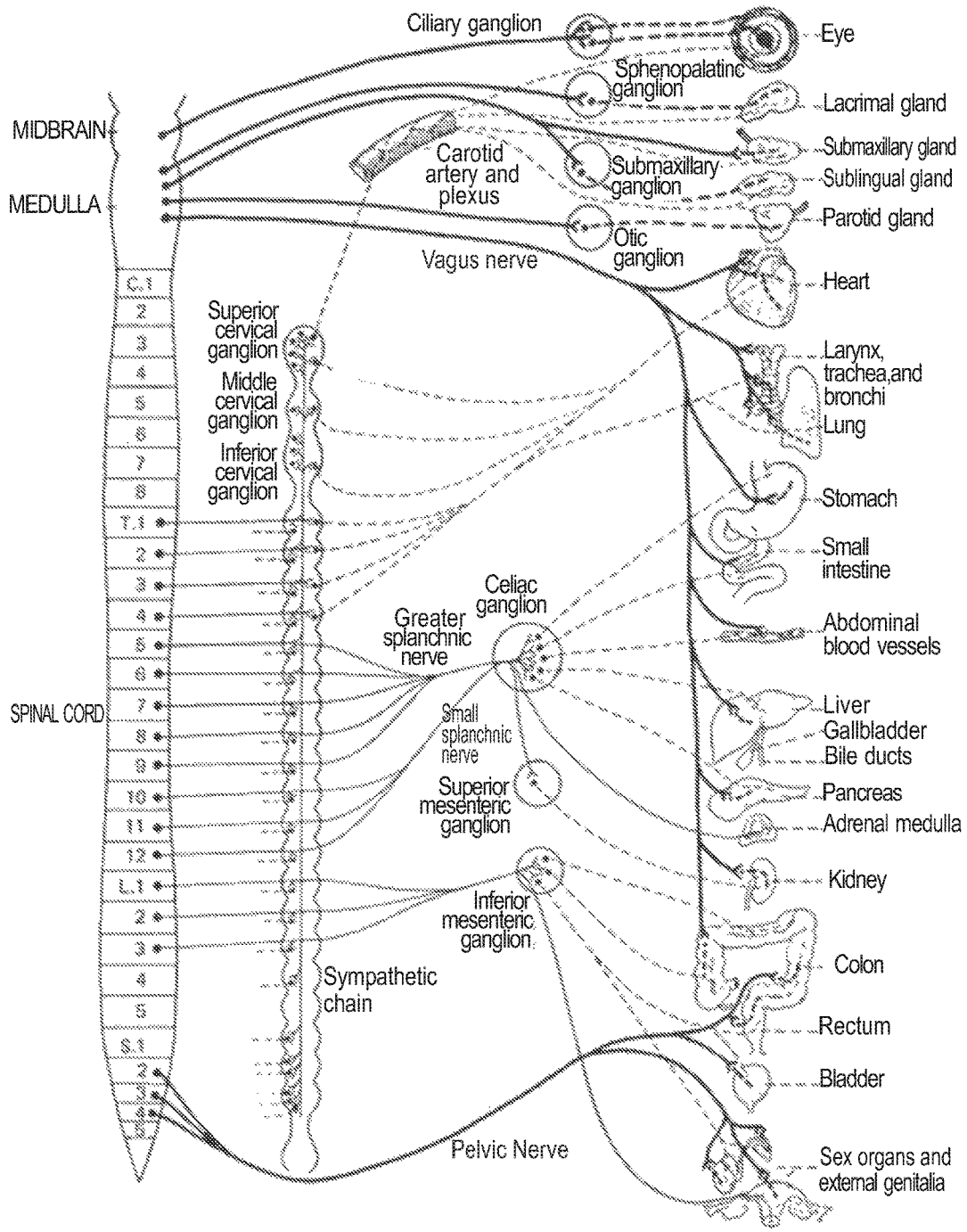
FIG. 5 is a conceptual illustration of the SNS and how the brain communicates with the body via the SNS.

As shown in FIG. 5, the SNS provides a network of nerves that allows the brain to communicate with the body. Sympathetic nerves originate inside the vertebral column, toward the middle of the spinal cord in the intermediolateral cell column (or lateral horn), beginning at the first thoracic segment of the spinal cord and are thought to extend to the second or third lumbar segments. Because its cells begin in the thoracic and lumbar regions of the spinal cord, the SNS is said to have a thoracolumbar outflow. Axons of these nerves leave the spinal cord through the anterior rootlet/root. They pass near the spinal (sensory) ganglion, where they enter the anterior rami of the spinal nerves. However, unlike somatic innervation, they quickly separate out through white rami connectors that connect to either the paravertebral (which lie near the vertebral column) or prevertebral (which lie near the aortic bifurcation) ganglia extending alongside the spinal column.

In order to reach the target organs and glands, the axons travel long distances in the body. Many axons relay their message to a second cell through synaptic transmission. The first cell (the presynaptic cell) sends a neurotransmitter across the synaptic cleft (the space between the axon terminal of the first cell and the dendrite of the second cell) where it activates the second cell (the postsynaptic cell). The message is then propagated to the final destination.

In the SNS and other neuronal networks of the peripheral nervous system, these synapses are located at sites called ganglia, discussed above. The cell that sends its fiber to a ganglion is called a preganglionic cell, while the cell whose fiber leaves the ganglion is called a postganglionic cell. As mentioned previously, the preganglionic cells of the SNS are located between the first thoracic (T1) segment and third lumbar (L3) segments of the spinal cord. Postganglionic cells have their cell bodies in the ganglia and send their axons to target organs or glands. The ganglia include not just the sympathetic trunks but also the cervical ganglia (superior, middle and inferior), which sends sympathetic nerve fibers to the head and thorax organs, and the celiac and mesenteric ganglia (which send sympathetic fibers to the gut).

2. Innervation of the Ovaries

Figure 6:
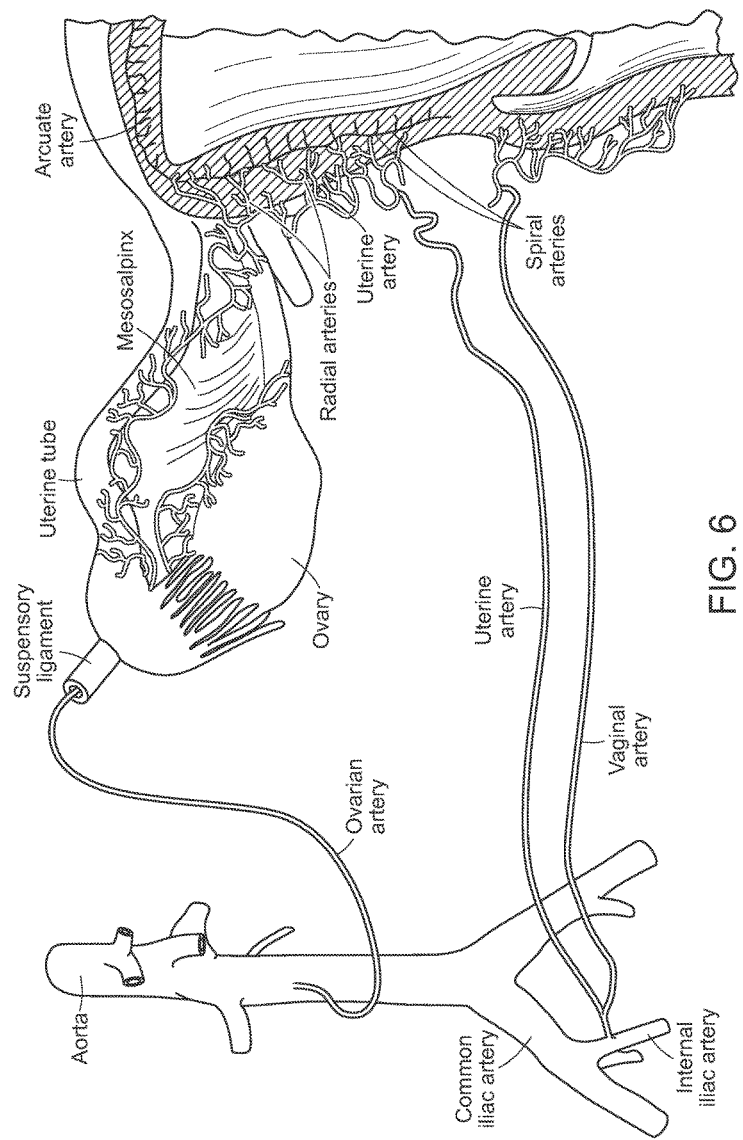
FIG. 6 is an enlarged anatomic view of arterial vasculature anatomy of a left ovary.

The ovaries and part of the fallopian tubes and broad ligament of the uterus are innervated by the ovarian plexus, a network of nerve fibers accompanying the ovarian vessels and derived from the aortic and renal plexuses. As FIG. 6 shows, the blood supply to the ovary is provided by the ovarian artery. The ovarian plexus is an autonomic plexus that surrounds the ovarian artery and is carried in the suspensory ligament. The ovarian plexus extends along the ovarian artery until it arrives at the substance of the ovary. Fibers contributing to the ovarian plexus arise from the renal plexus, celiac ganglion, the superior mesenteric ganglion, the aorticorenal ganglion and the aortic plexus. The ovarian plexus, also referred to as the ovarian nerve, is predominantly comprised of sympathetic nerve fibers.

Preganglionic neuronal cell bodies are located in the intermediolateral cell column of the spinal cord. Preganglionic axons pass through the paravertebral ganglia (they do not synapse) to become the lesser splanchnic nerve, the least splanchnic nerve, the first lumbar splanchnic nerve, and the second lumbar splanchnic nerve, and they travel to the celiac ganglion, the superior mesenteric ganglion, and the aorticorenal ganglion. Postganglionic neuronal cell bodies exit the celiac ganglion, the superior mesenteric ganglion, and the aorticorenal ganglion to the renal plexus, which are distributed to the renal vasculature, and give rise to the ovarian plexus which is distributed to the ovary and the fundus of the uterus.

3. Ovarian Sympathetic Neural Activity

Messages trawl through the SNS in a bidirectional flow. Efferent messages may trigger changes in different parts of the body simultaneously. For example, the SNS may accelerate heart rate; widen bronchial passages; decrease motility (movement) of the large intestine; constrict blood vessels; increase peristalsis in the esophagus; cause pupil dilation, cause piloerection (i.e., goose bumps), cause perspiration (i.e., sweating), and raise blood pressure. Afferent messages carry signals from various organs and sensory receptors in the body to other organs and, particularly, the brain.

Hypertension, heart failure and chronic kidney disease are a few of many disease states that result from chronic activation of the SNS, especially the renal sympathetic nervous system. Chronic activation of the SNS is a maladaptive response that drives the progression of these disease states. Pharmaceutical management of the renin-angiotensin-aldosterone system (RAM) has been a longstanding, but somewhat ineffective, approach for reducing overactivity of the SNS.

Some experimental data and clinical results are suggestive of the role the sympathetic nervous system has as a contributor to the complex pathophysiology of PCOS. For example, studies measuring efferent postganglionic MSNA in PCOS patients revealed that PCOS is associated with high MSNA. Elevated testosterone and cholesterol lipid levels were identified as independent predictors of MSNA in PCOS. Additional evidence suggests that there is a greater density of catecholaminergic nerve fibers in polycystic ovaries and altered peripheral catecholamine secretion in adolescent PCOS patients. It has also been shown that activation of the sympathetic neurons innervating the ovary precedes the development of cystic ovaries in rats.

VII. EXAMPLES

Example 1: Effect of Renal Neuromodulation on PCOS

This section describes an example of the outcome of renal neuromodulation on two patients diagnosed with PCOS and observed approximately three months following renal neuromodulation (Schlaich et al., 2011, Journal of Hypertension 29: 991-996; incorporated herein by reference in its entirety).

Two obese patients with hypertension and PCOS were offered to undergo a renal neuromodulation procedure. Prior to renal neuromodulation, patient 1 (27 years old) weighed 97.6 kg and had a BMI of 36.2 kg/m$^2$, and patient 2 (34 years old) weighted 90.4 kg and had a BMI of 34.3 kg/m$^2$. PCOS was previously diagnosed in both patients by a combination of clinical and biochemical signs of hyperandrogenism and polycystic ovaries on ultrasound imaging. Lifestyle and medication were stable for at least four weeks prior to the baseline assessment and the patients did not change their lifestyle and medication during the three months between the renal neuromodulation and the follow-up assessment. Following the baseline assessment of sympathetic nerve activity (using microneurography (MSNA) and norepinephrine spillover measurements) and insulin sensitivity (using euglycemic hyperinsulinemic clamp), both patients underwent bilateral radiofrequency renal neuromodulation without any periprocedural complications. Measurements of cystatin-C, creatinine clearance, and urinary albumin creatinine ratio were also obtained. All measurements performed at the baseline assessment were repeated three months after the renal neuromodulation at the follow-up assessment.

MSNA was recorded using microneurography in the peroneal nerve. A tracer infusion of 3H-labeled norepinephrine (levo-7-3HNE, specific activity of 11-25 Ci/mmol; New England Nuclear, Boston, Mass., USA) was given via a peripheral vein at 0.6-0.8 µCi/min, after a priming bolus of 12 µCi, for the measurement of total body norepinephrine spillover by isotope dilution. The euglycemic hyperinsulinemic clamp technique was used to quantify in-vivo insulin sensitivity. After a bolus injection of 9 mU/kg insulin (Actrapid HM100 U/ml; Novo Nordisk, Baulkham Hills, New South Wales, Australia), a constant infusion rate of 40 mU/m$^2$ per minute was maintained over two hours. Blood glucose concentration was clamped at the euglycemic level of 5 mmol/l through the variable infusion of 25% glucose and measured every 5 minutes using an autoanalyzer (ABL 800 Basic; Radiometer, Copenhagen). Peripheral insulin sensitivity was derived from the average glucose infusion rate during the final 20 minutes, corrected for glucose space, and normalized to body weight.

Figure 7A:
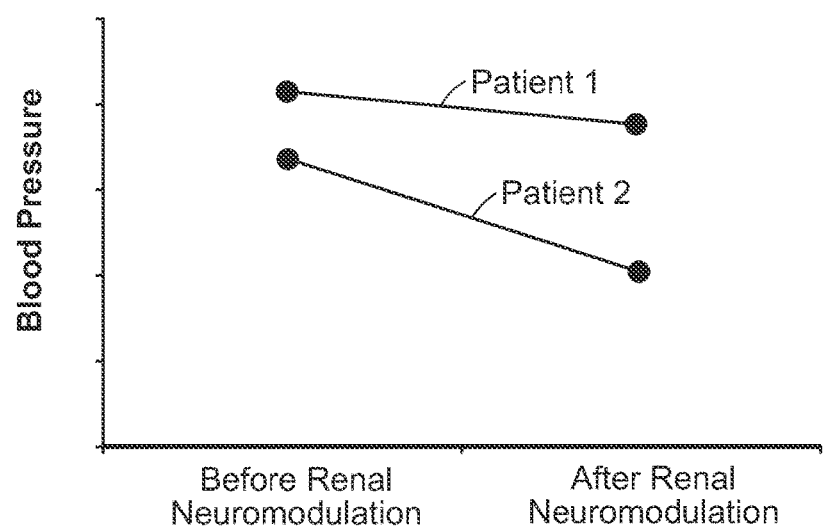
FIG. 7A is a plot of systolic office blood pressure (mmHg) at a baseline assessment and at 12 weeks after renal neuromodulation for two patients with polycystic ovary syndrome (PCOS).
Figure 7B:
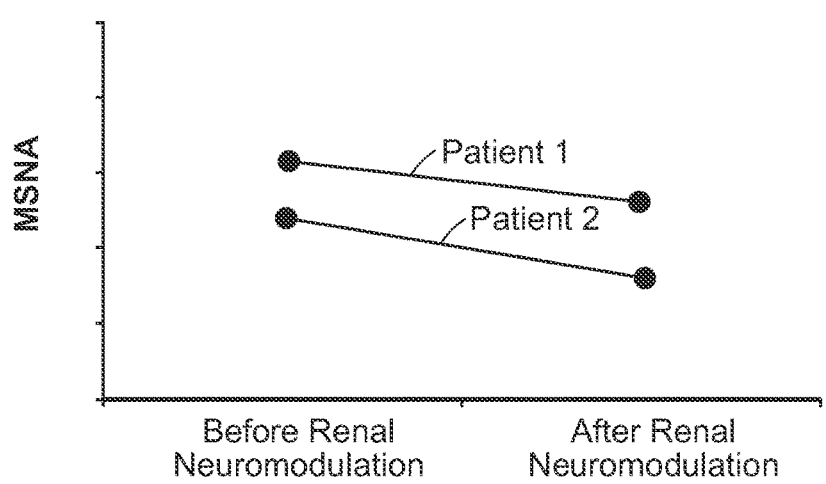
FIG. 7B is a plot of muscle sympathetic nerve activity (bursts per 100 heart beats) at a baseline assessment and at 12 weeks after renal neuromodulation for two patients with PCOS.
Figure 7C:
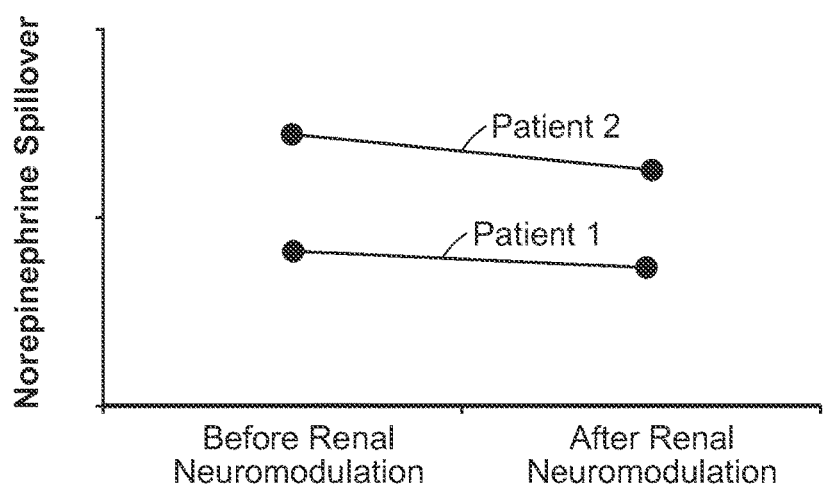
FIG. 7C is a plot of whole body norepinephrine spillover (ng/min) at a baseline assessment and at 12 weeks after renal neuromodulation for two patients with PCOS.

Both patients had uncontrolled clinic blood pressure levels at baseline (e.g., Patient 1 had a baseline blood pressure of 183/107 mmHg, Patient 2 had a baseline blood pressure of 167/123 mmHg) despite a therapeutic regimen consisting of at least four different antihypertensive drug classes and had a BMI in the obese range (FIG. 7A). For example, Patient 1 was taking a regimen of Irbesartan/HCT, Methyldopa, Prazosin and Spironolactone, and Patient 2 was taking a regimen of Spironolactone, Amlodipine/valsartan, Ramipril and Moxonidine. Of note, Patient 1 was intolerant to calcium channel blockers and Patient 2 to thiazide diuretics. Neither of the patients was on oral antidiabetic drugs or insulin before or during the study. Both patients had normal renal function as indicated by cystatin-C levels below 1 mg/l. As shown in FIGS. 79 and 7C, indices of sympathetic nervous system activation were substantially elevated in both patients with an approximately 2.5 to 3-fold increase above levels typically found in normotensive healthy controls for both MSNA (normal being about 15 to 20 burst/ min) and whole body norepinephrine (NE) spillover (normal being about 300 to 600 ng/min).

Bilateral renal neuromodulation resulted in mild-to-moderate reductions in systolic blood pressure and diastolic blood pressure in the two patients at the three-month follow-up (FIG. 7A). For example, 3 months post renal neuromodulation, Patient 1 had a blood pressure of 175/81 mmHg, and Patient 2 had a blood pressure of 140/102 mmHg. MSNA was reduced in both patients by about 17% and about 33%, respectively (FIG. 7B) after renal neuromodulation Whole body NE spillover was well above the upper normal limit of around 600 ng/min in both patients at baseline and reduced in both patients by 5% and 8% directly after renal neuromodulation (FIG. 7C), and by 28% in the one patient who had whole body NE spillover repeated at 12 weeks, suggesting that sympathetic activation may decrease further over time.

Figure 8A:
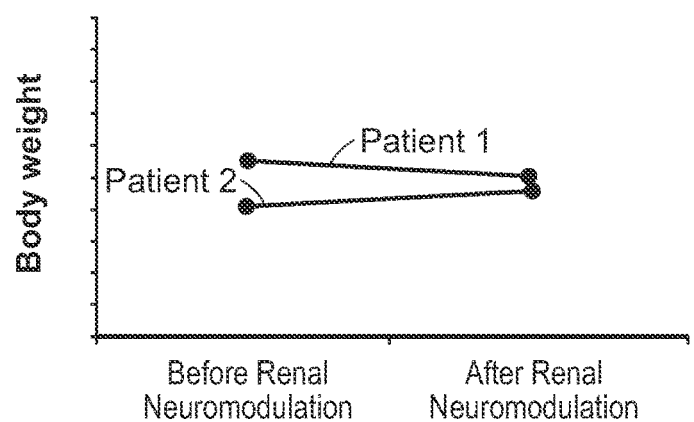
FIG. 8A is a plot of body weight (kg) at a baseline assessment and at 12 weeks after renal neuromodulation for two patients with PCOS.
Figure 8B:
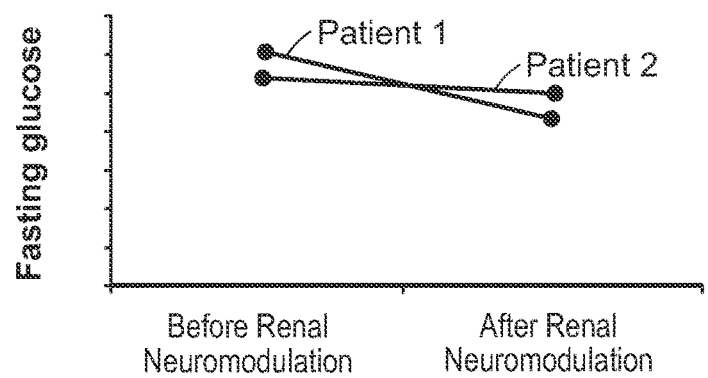
FIG. 8B is a plot of fasting plasma glucose (mmol/l) at a baseline assessment and at 12 weeks after renal neuromodulation for two patients with PCOS.
Figure 8C:
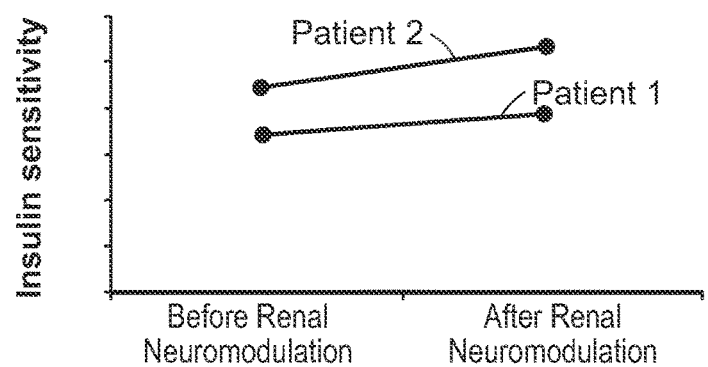
FIG. 8C is a plot of insulin sensitivity (mg/kg per) at a baseline assessment and at 12 weeks after renal neuromodulation for two patients with PCOS.
Figure 8D:
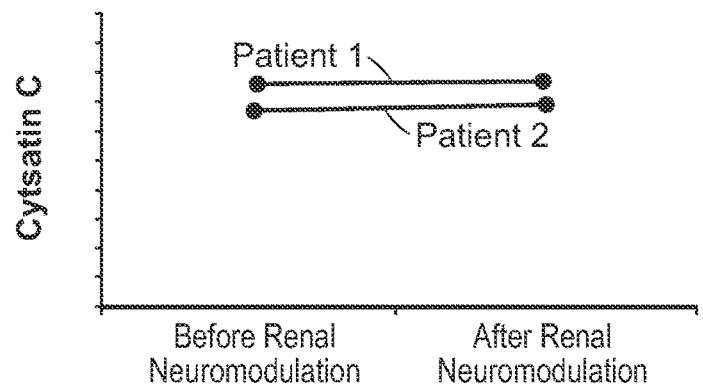
FIG. 8D is a plot of cystatin C (mg/l) at a baseline assessment and at 12 weeks after renal neuromodulation for two patients with PCOS.
Figure 8E:
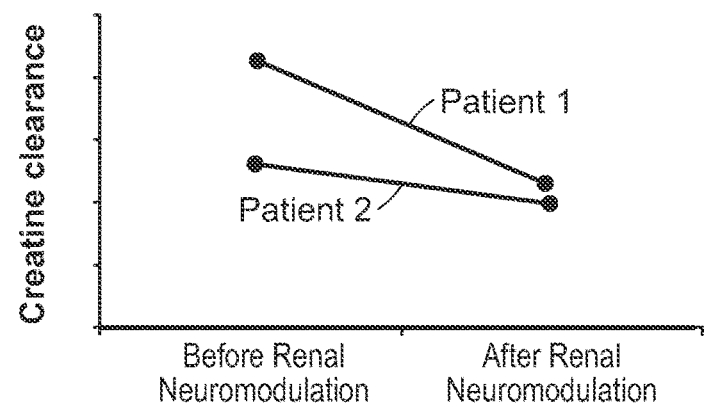
FIG. 8E is a plot of creatinine clearance (ml/min) at a baseline assessment and at 12 weeks after renal neuromodulation for two patients with PCOS.
Figure 8F:
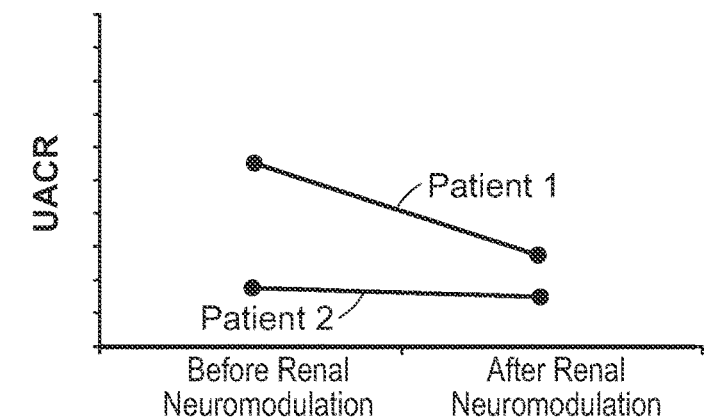
FIG. 8F is a plot of urinary albumin creatinine ratio (mg/g creatinine) at a baseline assessment and at 12 weeks after renal neuromodulation for two patients with PCOS.

Changes in metabolic parameters following bilateral renal neuromodulation are illustrated in FIGS. 8A-8F. There was no substantial change in body weight with Patient 1 experiencing a minor reduction (e.g., 2.5 kg reduction) and Patient 2 experiencing a minor increase (e.g., 2.4 kg increase) in body weight at the three-month follow-up (FIG. 8A). Fasting plasma glucose levels were lower in both patients at the three-month follow-up compared to baseline (FIG. 8B). Insulin sensitivity, as assessed by euglycemic hyperinsulinemic clamp, increased by 20.9% and 14.4%, respectively, in both patients at the three-month follow-up after renal neuromodulation (FIG. 8C). There was no indication of renal function impairment after renal neuromodulation with cystatin-C levels being unchanged or reduced (FIG. 8D). Assessment of creatinine clearance at baseline, though limited in accurately assessing glomerular filtration, revealed a state of hyperfiltration in Patient 1 (216 and 132 ml/min, respectively), which was normalized three months after renal neuromodulation (FIG. 8E). Patient 1 presented with microalbuminuria at baseline, which was substantially reduced by approximately 50% at the three-month follow-up after renal neuromodulation (FIG. 8F).

As discussed above, PCOS has been associated with increased sympathetic nerve activity. The reduction of central sympathetic drive associated with renal neuromodulation may highlight the relevance of sympathetic activation in blood pressure control and glucose metabolism in patients with PCOS. Indeed, sympathetic activation may be a link between obesity, hypertension, and insulin resistance, which are frequently encountered in PCOS and represent an important target for the prevention and treatment of the metabolic and cardiovascular features of PCOS. The findings discussed in this example suggest an inhibitory effect of renal neuromodulation on indices of sympathetic activation that was associated with simultaneous reduction in both blood pressure and insulin resistance. Similar findings on insulin resistance have been reported with pharmaceutical agents that reduce central sympathetic drive, such as moxonidine.

The findings suggest that reduction of sympathetic activity, as measured by MSNA and norepinephrine spillover, via renal sympathetic neuromodulation resulted in improved tasting glucose levels and insulin sensitivity in the absence of significant changes in body weight and any alterations in lifestyle or antihypertensive medication. A likely explanation for the substantial improvement in insulin sensitivity in response to renal neuromodulation is a combination of beneficial effects of sympatho inhibition and reduced re lease of norepinephrine on regional hemodynamics and direct cellular effects.

In the human forearm, increased norepinephrine release typically results in a substantial reduction in forearm blood flow (e.g., as measured by venous occlusion plethysmography) and typically is associated with a markedly reduced forearm uptake of glucose. This can highlight the adverse effect of sympathetic activation on the ability of the cell to transport glucose across its membrane, a hallmark of insulin resistance. This can be the result of a reduced number of open capillaries due to vasoconstriction and/or an increase in the distance that insulin must travel to reach the cell membrane from the intravascular compartment. Furthermore, this situation can be perpetuated if insulin resistance already exists, which can reduce the ability of insulin to increase muscle perfusion e.g., by approximately 30%). The relevance of these hemodynamic consequences of sympathetic activation is highlighted by studies demonstrating a direct relationship between the sympathetic nerve firing rate to skeletal muscle tissue and insulin resistance and an inverse relationship between insulin resistance and the number of open capillaries.

Although hormone levels were not measured, it is striking that one of the two patients who was amenorrheic for the previous 3 years resumed irregular menses approximately 6 weeks after the renal neuromodulation procedure. The findings discussed in this example suggest that a localized, single intervention specifically targeting the renal nerves may have beneficially influenced aspects of PCOS.

Example 2: Effect of Renal Neuromodulation on Hypertension

Patients were selected having a baseline systolic blood pressure of 160 mm Hg or more (≥150 mm Hg for patients with type 2 diabetes) and taking three or more antihypertensive drugs, and were randomly allocated into two groups: 51 assessed in a control group (antihypertensive drugs only) and 49 assessed in a treated group (undergone renal neuromodulation and antihypertensive drugs).

Patients in both groups were assessed at 6 months. Office-based blood pressure measurements in the treated group were reduced by 32/12 mm Hg (SD 23/11, baseline of 178/96 mm Hg, $p<0.0001$), whereas they did not differ from baseline in the control group (change of 1/0 mm Hg, baseline of 178/97 mm Hg, $p=0.77$ systolic and $p=0.83$ diastolic). Between-group differences in blood pressure at 6 months were 33/11 mm Hg ($p<0.0001$). At 6 months, 41 (84%) of 49 patients who underwent renal neuromodulation had a reduction in systolic blood pressure of 10 mm Hg or more, compared with 18 (35%) of 51 control patients ($p<0.0001$).

VIII. FURTHER EXAMPLES

1. A method of treating a human patient diagnosed with polycystic ovary syndrome, the method comprising:
   intravascularly positioning a neuromodulation assembly within an ovarian blood vessel of the patient and adjacent to an ovarian nerve of the patient; and
   reducing sympathetic neural activity in the patient by delivering energy to the ovarian nerve via the neuromodulation assembly to modulate the ovarian nerve,
   wherein reducing sympathetic neural activity improves a measurable physiological parameter corresponding to the polycystic ovary syndrome of the patient.

2. The method of example 1 wherein reducing sympathetic neural activity in the patient in a manner that improves a measurable physiological parameter corresponding to the polycystic ovary syndrome comprises reducing expansion of, maintaining the size of or reducing the size of an ovarian cyst in the patient.

3. The method of example 1 or example 2 wherein reducing sympathetic neural activity in the patient in a manner that improves a measurable physiological parameter corresponding to the polycystic ovary syndrome comprises reducing the size of an ovarian cyst in the patient at least about 5% within about three months to about 12 months after reducing sympathetic neural activity in the patient by delivering energy to the ovarian nerve.

4. The method of any one of examples 1-3 wherein reducing sympathetic neural activity in the patient in a manner that improves a measurable physiological parameter corresponding to the polycystic ovary syndrome comprises reducing a number of ovarian cysts in the patient at least about 5% within about three months to about 12 months after reducing sympathetic neural activity in the patient by delivering energy to the ovarian nerve.

5. The method of any one of examples 1-4 wherein reducing sympathetic neural activity in the patient in a manner that improves a measurable physiological parameter corresponding to the polycystic ovary syndrome comprises reducing muscle sympathetic nerve activity in the patient.

6. The method of any one if examples 1-5 wherein reducing sympathetic neural activity in the patient in a manner that improves a measurable physiological parameter corresponding to the polycystic ovary syndrome comprises reducing whole body norepinephrine spillover in the patient.

7. The method of any one of examples 1-6 wherein reducing sympathetic neural activity in the patient in a manner that improves a measurable physiological parameter corresponding to the polycystic ovary syndrome comprises reducing ovarian norepinephrine spillover to plasma in the patient.

8. The method of any one of examples 1-7 wherein the polycystic ovary syndrome is associated with a condition including oligo/amenorrhea, and wherein reducing sympathetic neural activity in the patient in a manner that improves a measurable physiological parameter corresponding to the polycystic ovary syndrome comprises causing resumption of menses in the patient within about three months to about 12 months after reducing sympathetic neural activity in the patient by delivering energy to the ovarian nerve.

9. The method of any one of examples 1-8 wherein reducing sympathetic neural activity in the patient by delivering energy to the ovarian nerve comprises at least partially inhibiting afferent neural activity.

10. The method of any one of examples 1-9 wherein reducing sympathetic neural activity in the patient by delivering energy to the ovarian nerve comprises at least partially inhibiting efferent neural activity.

11. The method of any one of examples 11-10 wherein reducing sympathetic neural activity in the patient by delivering energy to the ovarian nerve comprises modulating the ovarian nerve of the patient via an intravascularly positioned catheter carrying a neuromodulation assembly positioned at least proximate to the ovarian nerve.

12. The method of any one of examples 1-11 wherein modulating the ovarian nerve includes thermally modulating the ovarian nerve from within the ovarian artery of the patient.

13. The method of example 12 wherein thermally modulating the ovarian nerve includes cryotherapeutically cooling the ovarian nerve.

14. The method of example 12 or example 13 wherein thermally modulating the ovarian nerve includes delivering an energy field to the ovarian nerve.

15. A method, comprising:
    percutaneously introducing a neuromodulation assembly at a distal portion of a treatment device proximate to neural fibers innervating an ovary of a human patient diagnosed with polycystic ovary syndrome or infertility;
    partially disrupting function of the neural fibers innervating the ovary by applying thermal energy to the neural fibers via the neuromodulation assembly; and
    removing the neuromodulation assembly from the patient after treatment,
    wherein partial disruption of the function of the neural fibers innervating the ovary therapeutically treats the diagnosed polycystic ovary syndrome or infertility.

16. The method of example 15 wherein the patient is diagnosed with polycystic ovary syndrome, and wherein the method further comprises improving one or more physiological parameters corresponding to the polycystic ovary syndrome.

17. The method of example 16 wherein improving one or more physiological parameters corresponding to the polycystic ovary syndrome includes reducing at least one of androgen levels, lipid levels, blood pressure, acne and hirsutism.

18. The method of any one of examples 15-17 wherein the patient is diagnosed with infertility, and wherein partial disruption of the function of the neural fibers reverses infertility in the patient.

19. A method for treating polycystic ovary syndrome in a human patient, the method comprising:
    positioning an energy delivery element of an ovarian denervation catheter within an ovarian blood vessel of the patient and adjacent to post-ganglionic neural fibers that innervate an ovary of the patient; and
    at least partially ablating the neural fibers innervating the ovary of the patient via the energy delivery element,
    wherein at least partially ablating the neural fibers innervating the ovary results in a therapeutically beneficial reduction in one or more physiological conditions associated with polycystic ovary syndrome of the patient.

20. The method of example 19, further comprising administering one or more pharmaceutical drugs to the patient, wherein the pharmaceutical drugs are selected from the group consisting of antihypertensive drugs, hormone therapy drugs and anti-diabetic drugs.

21. The method of example 19 or example 20 wherein the reduction in one or more physiological conditions associated with polycystic ovary syndrome includes a reduction in the number of ovarian cysts in the patient.

IX. CONCLUSION

The above detailed descriptions of embodiments of the technology are not intended to be exhaustive or to limit the technology to the precise form disclosed above. Although specific embodiments of and examples for, the technology are described above for illustrative purposes, various equivalent modifications are possible within the scope of the technology, as those skilled in the relevant art will recognize. For example, while steps are presented in a given order, alternative embodiments may perform steps in a different order. For example, in additional embodiments, the system 100 may include a treatment device configured to deliver therapeutic energy to the patient from an external location outside the patient's body, i.e., without direct or close contact to the target site. The various embodiments described herein may also be combined to provide further embodiments.

From the foregoing, it will be appreciated that specific embodiments of the technology have been described herein for purposes of illustration, but well-known structures and functions have not been shown or described in detail to avoid unnecessarily obscuring the description of the embodiments of the technology. Where the context permits, singular or plural terms may also include the plural or singular term, respectively.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

I claim:

1. A method of treating a human patient diagnosed with polycystic ovary syndrome, the method comprising:
    intravascularly positioning a neuromodulation assembly within an ovarian blood vessel of the human patient and adjacent to an ovarian nerve of the human patient; and
    reducing ovarian sympathetic neural activity in the human patient by delivering energy to the ovarian nerve via the neuromodulation assembly to modulate the ovarian nerve,
    wherein reducing the ovarian sympathetic neural activity reduces expansion of, maintains the size of, or reduces the size of an ovarian cyst in the human patient diagnosed with polycystic ovary syndrome.

2. The method of claim 1 wherein reducing the ovarian sympathetic neural activity in the human patient reduces the size of an ovarian cyst in the human patient at least by about 5% within about three months to about 12 months after reducing the ovarian sympathetic neural activity in the human patient by delivering energy to the ovarian nerve.

3. The method of claim 1 wherein reducing the sympathetic neural activity in the human patient further reduces a number of ovarian cysts in the human patient at least by about 5% within about three months to about 12 months after reducing the ovarian sympathetic neural activity in the human patient by delivering energy to the ovarian nerve.

4. The method of claim 1 wherein reducing the ovarian sympathetic neural activity in the human patient further reduces muscle sympathetic nerve activity in the human patient.

5. The method of claim 1 wherein reducing the ovarian sympathetic neural activity in the human patient further reduces whole body norepinephrine spillover in the human patient.

6. The method of claim 1 wherein reducing the ovarian sympathetic neural activity in the human patient further reduces ovarian norepinephrine spillover to plasma in the human patient.

7. The method of claim 1 wherein the polycystic ovary syndrome is associated with a condition including oligo/amenorrhea, and wherein reducing the ovarian sympathetic neural activity in the human patient further causes resumption of menses in the human patient within about three months to about 12 months after reducing the ovarian sympathetic neural activity in the human patient by delivering energy to the ovarian nerve.

8. The method of claim 1 wherein reducing the ovarian sympathetic neural activity in the human patient by delivering energy to the ovarian nerve comprises at least partially inhibiting afferent neural activity.

9. The method of claim 1 wherein reducing the ovarian sympathetic neural activity in the human patient by delivering energy to the ovarian nerve comprises at least partially inhibiting efferent neural activity.

10. The method of claim 1 wherein reducing the ovarian sympathetic neural activity in the human patient by delivering energy to the ovarian nerve comprises modulating the ovarian nerve of the human patient via an intravascularly positioned catheter carrying a neuromodulation assembly positioned at least proximate to the ovarian nerve.

11. The method of claim 10 wherein modulating the ovarian nerve includes thermally modulating the ovarian nerve from within the ovarian blood vessel of the human patient.

12. The method of claim 11 wherein thermally modulating the ovarian nerve includes cryotherapeutically cooling the ovarian nerve.

13. The method of claim 11 wherein thermally modulating the ovarian nerve includes delivering an energy field to the ovarian nerve.

14. A method, comprising:
    percutaneously introducing a neuromodulation assembly at a distal portion of a treatment device within an ovarian artery proximate to neural fibers innervating an ovary of a human patient diagnosed with polycystic ovary syndrome;
    at least partially disrupting function of the neural fibers innervating the ovary by applying thermal energy to the neural fibers innervating the ovary via the neuromodulation assembly; and
    removing the neuromodulation assembly from the human patient after treatment,
    wherein at least partial disruption of the function of the neural fibers innervating the ovary reduces a number of ovarian cysts in the human patient.

15. The method of claim 14 wherein at least partial disruption of the function of the neural fibers innervating the ovary further provides an improvement in one or more endocrine hormone levels in the human patient diagnosed with polycystic ovary syndrome.

16. The method of claim 14 wherein at least partial disruption of the function of the neural fibers innervating the ovary further reduces at least one of lipid levels, blood pressure, acne and hirsutism.

17. The method of claim 14 wherein the human patient is further diagnosed with infertility, and wherein at least partial disruption of the function of the neural fibers innervating the ovary reverses infertility in the human patient.

18. The method of claim 15 wherein the improvement in one or more endocrine hormone levels in the human patient includes a reduction in an androgen level in the human patient.

19. A method for treating polycystic ovary syndrome in a human patient, the method comprising:
    positioning an energy delivery element of an ovarian denervation catheter within an ovarian blood vessel of the human patient and adjacent to post-ganglionic neural fibers that innervate an ovary of the human patient; and
    at least partially ablating the post-ganglionic neural fibers innervating the ovary of the human patient via the energy delivery element,
    wherein at least partially ablating the post-ganglionic neural fibers innervating the ovary results in a therapeutically beneficial reduction in the expansion of or the size of one or more ovarian cysts in the human patient having polycystic ovary syndrome.

20. The method of claim 19, further comprising administering one or more pharmaceutical drugs to the human patient, wherein the pharmaceutical drugs are selected from the group consisting of antihypertensive drugs, hormone therapy drugs and anti-diabetic drugs.

21. The method of claim 19 wherein at least partially ablating the post-ganglionic neural fibers innervating the ovary further reduces a number of ovarian cysts in the human patient.

22. The method of claim 19 wherein the ovarian denervation catheter is a 3 French or 4 French catheter.

* * * * *